United States Patent
Yang et al.

(10) Patent No.: US 8,236,091 B2
(45) Date of Patent: Aug. 7, 2012

(54) FLUID SEPARATION METHOD AND FLUID SEPARATION APPARATUS

(75) Inventors: Sheng-Chiang Yang, Taipei (TW);
Shih-Chi Lu, Taipei County (TW);
Bing-Joe Hwang, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 483 days.

(21) Appl. No.: 12/534,860

(22) Filed: Aug. 4, 2009

(65) Prior Publication Data
US 2010/0307334 A1 Dec. 9, 2010

(30) Foreign Application Priority Data
Jun. 9, 2009 (TW) ................................ 98119234 A

(51) Int. Cl.
*B08B 3/00* (2006.01)
(52) U.S. Cl. ............. 95/183; 55/385.1; 55/385.2; 95/90;
95/186; 95/236; 134/1; 134/2; 134/95.1;
134/95.3; 134/109; 134/110; 134/111; 134/195
(58) Field of Classification Search ................. 55/385.1,
55/385.2; 95/90, 183, 186, 236; 134/1, 2,
134/95.1, 95.3, 109, 110, 111, 195
See application file for complete search history.

(56) References Cited

U.S. PATENT DOCUMENTS

| 5,377,705 A | * | 1/1995 | Smith et al. | 134/95.3 |
| 5,494,526 A | * | 2/1996 | Paranjpe | 134/1 |
| 5,908,510 A | * | 6/1999 | McCullough et al. | 134/2 |
| 2004/0025908 A1 | * | 2/2004 | Douglas et al. | 134/56 R |
| 2010/0291763 A1 | * | 11/2010 | Ogawa et al. | 438/584 |

* cited by examiner

*Primary Examiner* — Robert A Hopkins
*Assistant Examiner* — Minh-Chau Pham
(74) *Attorney, Agent, or Firm* — Jianq Chyun IP Office

(57) ABSTRACT

A fluid separation apparatus suitable for separating a mixed fluid with different properties and capable of separating a complex fluid mixture efficiently is provided. The fluid separation apparatus includes a sampling entrance, a first separation column, a second separation column, a bypass line, a detector and a guide multi-channel valve. A mixed fluid flows into the first separation column via the sampling entrance. The second separation column is connected to the first separation column in series and connected to the bypass line in parallel. The detector is connected to the second separation column and the bypass line. The guide multi-channel valve has different modes to control a flow-through status and a closed status between the first separation column and the second separation column, between the first separation column and the bypass line, between the second separation column and the detector, and between the bypass line and the detector.

22 Claims, 17 Drawing Sheets

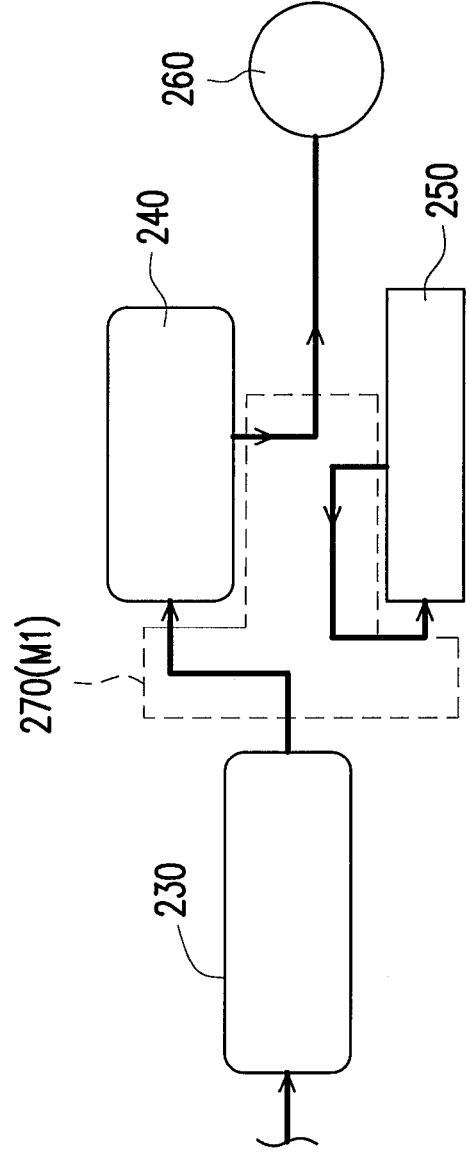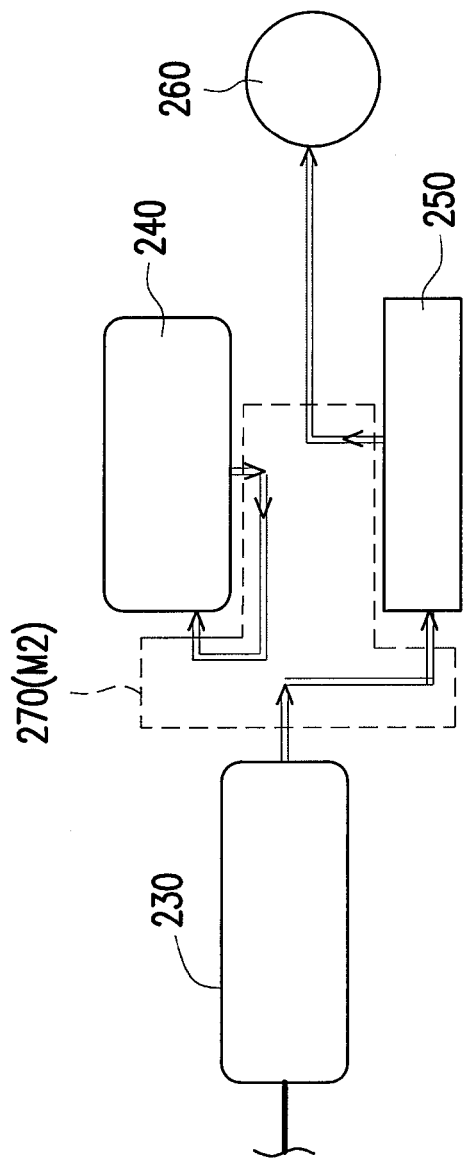

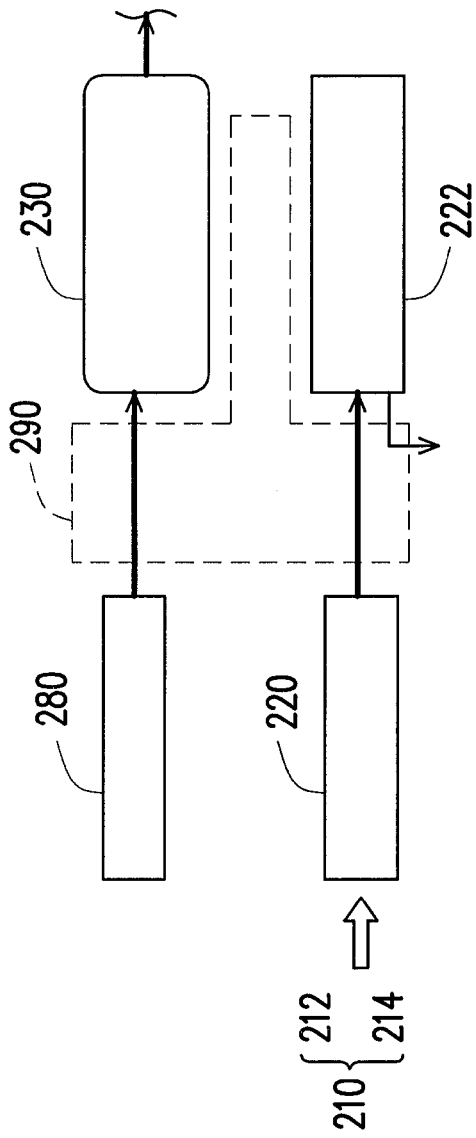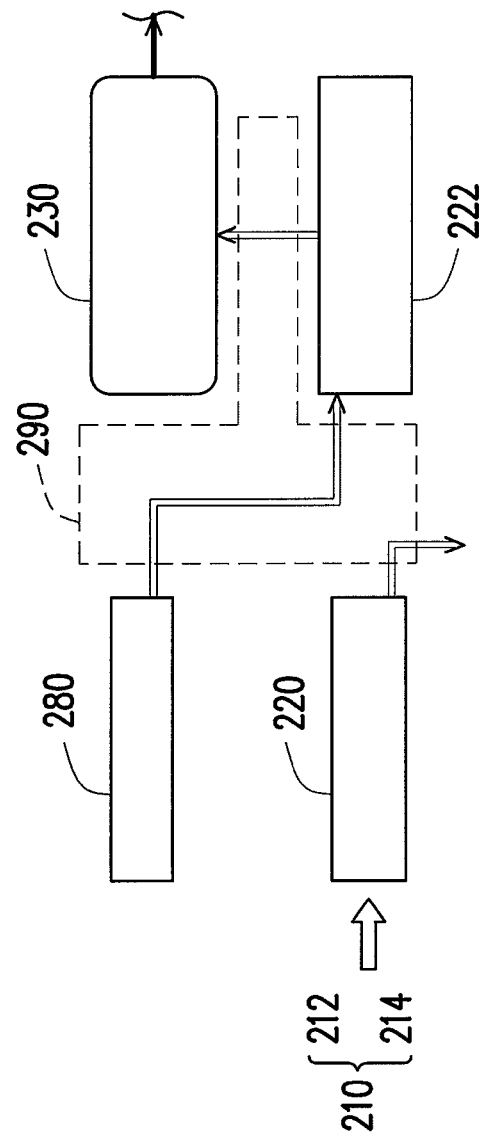

370(M2)

370(M1)

FLUID SEPARATION METHOD AND FLUID SEPARATION APPARATUS

CROSS-REFERENCE TO RELATED APPLICATION

This application claims the priority benefit of Taiwan application serial no. 98119234, filed Jun. 9, 2009. The entirety of the above-mentioned patent application is hereby incorporated by reference herein and made a part of specification.

BACKGROUND OF THE INVENTION

1. Field of the Invention

The present invention generally relates to a fluid separation method and a fluid separation apparatus, in particular, to a fluid separation method and a fluid separation apparatus capable of highly efficiently separating a complex fluid mixture.

2. Description of Related Art

In the past, during the manufacturing process of semiconductor integrated circuits, liquid crystal panels, solar cell panels, and magnetic devices etc., various different gases or liquids are usually used according to product types and manufacturing flows. For example, in a dry etching step or thin film forming step, various gases, for example, $CF_4$, $NF_3$, $C_3F_8$, $SF_6$, and $CHF_3$, are used as reactive gases, which contact the atmosphere when being exhausted, so as to probably generate the exhaust gas including $H_2$, $O_2$, $N_2$, $CH_4$, $CO$, $CO_2$, and $H_2O$ etc. In addition, with the rapid development of the industry, various gases are mixed together and cannot be completely separated and analyzed respectively In this manner, the gases not only encounter a bottleneck in waste disposal, but the gases are also hard to be analyzed if they cannot be efficiently separated, which thus result in burdens of a manufacturing cost and a waste disposal cost. Furthermore, components of the mixed fluid cannot be analyzed, which also causes potential risks.

For example, in the prior art, when a mixed gas including, for example, $CO_2$, $H_2O$, $CH_3OH$, $C_2H_5OH$, $H_2$, $O_2$, $N_2$, $CH_4$, and CO with different properties is to be separated, the chemical component of particles filled in a conventional separation column one is, calcium aluminum silicate, and an aperture thereof is approximately 5 Å, divalent calcium ions may generate extremely strong ionic bonds with polar molecules, for example, $H_2O$, $CH_3OH$, and $C_2H_5OH$, and the divalent calcium ions may generate ionic bonds with low polar molecules, for example, $CO_2$ and $H_2S$, such that the polar molecules easily block the separation column one, and even damage the separation column one.

Non-polar gas molecules with a size smaller than 5 Å may diffuse and enter pores, so as to be absorbed by the separation column one. On the other aspect, non-polar gas molecules with a size greater than 5 Å cannot diffuse and enter the pores, so as to be rejected outside the separation column one. In this manner, the separation column may perform the gas separation by using a physical property of the size of the gas molecules. Therefore, in the prior art, $H_2$, $O_2$, $N_2$, $CH_4$, and CO may be separated by the separation column one, and a separation column two is further disposed to separate the polar gas molecules of $CO_2$, $H_2O$, $CH_3OH$, and $C_2H_5OH$. However, the separation column two in the prior art cannot completely separate the following two types of gases of $H_2$, $O_2$, and $N_2$, and $CH_4$ and CO.

In the separation technique for separating the above conventional mixed gases, in order to prevent the polar molecules from generating the ionic bonds in the separation column one to damage the separation column one, the separation columns one and two must be installed in parallel in the prior art, so as to protect the separation column one from being damaged by the polar molecules. Furthermore, in order to further prevent the separation column one from being affected by the polar molecules, a $CO_2$ removal device and a condenser usually need to be added before the separation column one, so as to prevent a polar fluid from flowing into the separation column one to result in damages. Therefore, in the conventional gas separation technique, a detector needs to be added after the separation columns one and two respectively. In this manner, not only a cost and an occupied space of a separation apparatus are increased, but also the separation apparatus has no economic benefit.

SUMMARY OF THE INVENTION

Accordingly, the present invention is directed to a fluid separation method, which is capable of highly efficiently separating each component in a mixed fluid.

The present invention is further directed to a fluid separation apparatus, which is capable of highly efficiently separating each component in a mixed fluid by using a simple apparatus.

As embodied and broadly described herein, the present invention provides a fluid separation method, which includes the following steps. First, a mixed fluid with different properties is provided, in which the mixed fluid at least includes a first fluid and a second fluid, and the first fluid and the second fluid have different properties. Next, the mixed fluid is provided via a sampling entrance, and then the mixed fluid flows to a first separation column, in which the first fluid in the mixed fluid performs a separation procedure in the first separation column. Then, the second fluid in the mixed fluid flows to a second separation column connected to the first separation column in series through a guide multi-channel valve, in which the second fluid performs a separation procedure in the second separation column, and at this time, the guide multi-channel valve is in a first mode. The guide multi-channel valve is switched to a second mode, such that the second fluid is trapped within the second separation column, and the first fluid separated by the first separation column flows through a bypass line connected to the first separation column in series via the guide multi-channel valve, and is detected by a detector connected to the bypass line in series, in which the bypass line is connected to the second separation column in parallel. Then, the guide multi-channel valve is switched to the first mode, such that the second fluid trapped within the second separation column and already separated by the second separation column is delivered to the same detector via the guide multi-channel valve for being detected.

In an embodiment of the present invention, when the guide multi-channel valve is in the first mode, communication between the first separation column and the bypass line is in a closed status; communication between the first separation column and the second separation column, and communication between the second separation column and the detector are in a flow-through status; and the bypass line is in a loop closed status.

In an embodiment of the present invention, when the guide multi-channel valve is in the second mode, communication between the first separation column and the second separation column is, for example, in a closed status; communication between the first separation column and the bypass line, and communication between the bypass line and the detector are, for example, in a flow-through status; and the second separation column is, for example, in a loop closed status.

In an embodiment of the present invention, the process of providing the mixed fluid to the first separation column via the sampling entrance includes the following steps. First, a sampling loop, a carrier gas, and a sampling multi-channel valve are disposed, in which the sampling loop is connected between the sampling entrance and the first separation column, the mixed fluid is delivered in a direction from the sampling entrance to the detector through the carrier gas, and the sampling multi-channel valve is, for example, disposed between the first separation column and the sampling entrance. Then, the sampling multi-channel valve is switched to a sample inlet mode, and the mixed fluid filled in the sampling loop is delivered to the first separation column through the carrier gas. Particularly, when the sampling multi-channel valve is in the sample inlet mode, communication between the sampling entrance and the sampling loop is, for example, in a closed status; communication between the carrier gas and the sampling loop, and communication between the sampling loop and the first separation column are, for example, in a flow-through status; and the carrier gas flows from the sampling loop towards the first separation column. On the other aspect, the sampling multi-channel valve further includes a preset sampling mode, and when the sampling multi-channel valve is in the preset sampling mode, the mixed fluid flows in a flowing direction, for example, from the sampling entrance to the sampling loop, and the mixed fluid is filled in the sampling loop. Particularly, when the sampling multi-channel valve is in the preset sampling mode, communication between the sampling entrance and the sampling loop is, for example, in a flow-through status; communication between the sampling entrance and the first separation column is, for example, in a closed status; and the carrier gas flows from an entrance of the first separation column towards the detector.

In an embodiment of the present invention, the first fluid, for example, does not flow through the second separation column.

In an embodiment of the present invention, the first fluid includes a polar gas of a group consisting of $CO_2$ and $H_2O$, and the second fluid includes a non-polar gas of $H_2$.

In an embodiment of the present invention, the fluid separation method further includes the following steps. First, before the guide multi-channel valve is switched from the first mode to the second mode, a first part of the second fluid that is separated earlier is enabled to flow to the detector through the guide multi-channel valve in the first mode for being detected. Then, before a first part of the first fluid that is separated earlier enters the second separation column, the guide multi-channel valve is switched to the second mode, such that the first part of the first fluid that is separated earlier by the first separation column is detected by the detector through the guide multi-channel valve in the second mode, and a second part of the second fluid is left in the second separation column for performing the separation procedure during this period of time while the guide multi-channel valve in this second mode. Next, the guide multi-channel valve is switched to the first mode, and at this time, a second part of the first fluid is still left in the first separation column and performs the separation procedure during this period of time while the guide multi-channel valve in this first mode. Then, the second part of the second fluid left in the second separation column and already separated by the second separation column is delivered to the same detector through the guide multi-channel valve in the first mode for being detected. Afterwards, the guide multi-channel valve is switched to the second mode, and the second part of the first fluid left in the first separation column and already separated by the first separation column is delivered to the same detector through the guide multi-channel valve in the second mode for being detected during this period of time while the guide multi-channel valve in this second mode.

In an embodiment of the present invention, the process of enabling the second part of the second fluid to perform the separation procedure in the second separation column further includes performing a heating-up procedure.

In an embodiment of the present invention, the first fluid includes a polar gas of a group consisting of $CO_2$, $H_2O$, $CH_3OH$, and $C_2H_5OH$, and the second fluid includes a non-polar gas of $H_2$, $O_2$, $N_2$, $CH_4$, and CO. The first part of the first fluid is $CO_2$, and the second part of the first fluid is $H_2O$, $CH_3OH$, and $C_2H_5OH$. The first part of the second fluid is $H_2$, $O_2$, and $N_2$, and the second part of the second fluid is $CH_4$ and CO.

The present invention further provides a fluid separation apparatus, suitable for separating a mixed fluid with different properties, in which the mixed fluid at least includes a first fluid and a second fluid with different properties. The fluid separation apparatus includes a sampling entrance, a first separation column, a second separation column, a bypass line, a detector and a guide multi-channel valve. The mixed fluid flows into the fluid separation apparatus via the sampling entrance. The first separation column is connected to the sampling entrance, and used for separating the first fluid. The second separation column is connected to the first separation column in series, and used for separating the second fluid. The bypass line is connected to the second separation column in parallel, and connected to the first separation column in series. The detector is connected to the second separation column and the bypass line, and used for detecting the first fluid and the second fluid after the first fluid and the second fluid are separated. The guide multi-channel valve has different modes to control a flow-through status and a closed status between the first separation column and the second separation column, between the first separation column and the bypass line, between the second separation column and the detector, and between the bypass line and the detector.

In an embodiment of the present invention, the guide multi-channel valve has, for example, a first mode and a second mode. When the guide multi-channel valve is in the first mode, the mixed fluid flows in a flowing direction from the first separation column to the detector through the second separation column, and when the guide multi-channel valve is in the second mode, the mixed fluid flows in a flowing direction from the first separation column to the detector through the bypass line.

In an embodiment of the present invention, when the guide multi-channel valve is in the first mode, communication between the first separation column and the bypass line is, for example, in the closed status; communication between the first separation column and the second separation column, and communication between the second separation column and the detector are, for example, in the flow-through status; and the bypass line is, for example, in a loop closed status.

In an embodiment of the present invention, when the guide multi-channel valve is in the second mode, communication between the first separation column and the second separation column is, for example, in the closed status; communication between the first separation column and the bypass line, and communication between the bypass line and the detector are, for example, in the flow-through status; and the second separation column is, for example, in a loop closed status.

In an embodiment of the present invention, the fluid separation apparatus further includes a sampling loop and a carrier gas, in which the sampling loop is connected between the sampling entrance and the first separation column, and the mixed fluid is delivered in a direction from the sampling entrance to the detector through the carrier gas. In addition, the fluid separation apparatus is further selectively provided with a sampling multi-channel valve, which is disposed between the first separation column and the sampling entrance, and respectively controls communication between the sampling loop and the first separation column, communication between the sampling entrance and the sampling loop, communication between the carrier gas and the first separation column, and communication between the carrier gas and the sampling loop is in a flow-through status or a closed status. Particularly, the sampling multi-channel valve has, for example, a preset sampling mode and a sample inlet mode. When the sampling multi-channel valve is in the preset sampling mode, the mixed fluid flows in a flowing direction from the sampling entrance to the sampling loop, and the mixed fluid is filled in the sampling loop; and when the sampling multi-channel valve is in the sample inlet mode, the mixed fluid filled in the sampling loop is delivered to the first separation column through the carrier gas. Particularly, when the sampling multi-channel valve is in the preset sampling mode, communication between the sampling entrance and the sampling loop is in the flow-through status; communication between the sampling entrance and the first separation column is in the closed status; and the carrier gas flows in a direction from an entrance of the first separation column to the detector. On the other aspect, when the sampling multi-channel valve is in the sample inlet mode, communication between the sampling entrance and the sampling loop are in the closed status; communication between the carrier gas and the sampling loop, and communication between the sampling loop and the first separation column are in the flow-through status; and the carrier gas flows in a direction from the sampling loop to the first separation column.

In an embodiment of the present invention, the first fluid and the second fluid are respectively a polar gas and a non-polar gas. The first separation column is a separation column for separating the polar gas, and the second separation column is a separation column for separating the non-polar gas.

In view of the above, in the fluid separation method and the fluid separation apparatus according to the present invention, a single detector is adopted to highly efficiently separate the mixed fluid. Furthermore, a guide multi-channel valve is appropriately arranged, which saves the cost and occupied space of the apparatus, so that the complex fluid mixture can be efficiently separated and analyzed without an additional condenser. The present invention provides a novel fluid separation method and a novel fluid separation apparatus, so as to highly efficiently separate and analyze the fluid.

In order to make the aforementioned features and advantages of the present invention comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 3A and 3B are schematic views of external pipelines respectively corresponding to connection relations between the guide multi-channel valve and other members of FIGS. 2A and 2B.

FIGS. 6A and 6B are schematic views of external pipelines respectively corresponding to connection relations between the sampling multi-channel valve and other members of FIGS. 5A and 5B.

DESCRIPTION OF THE EMBODIMENTS

Figure 1:
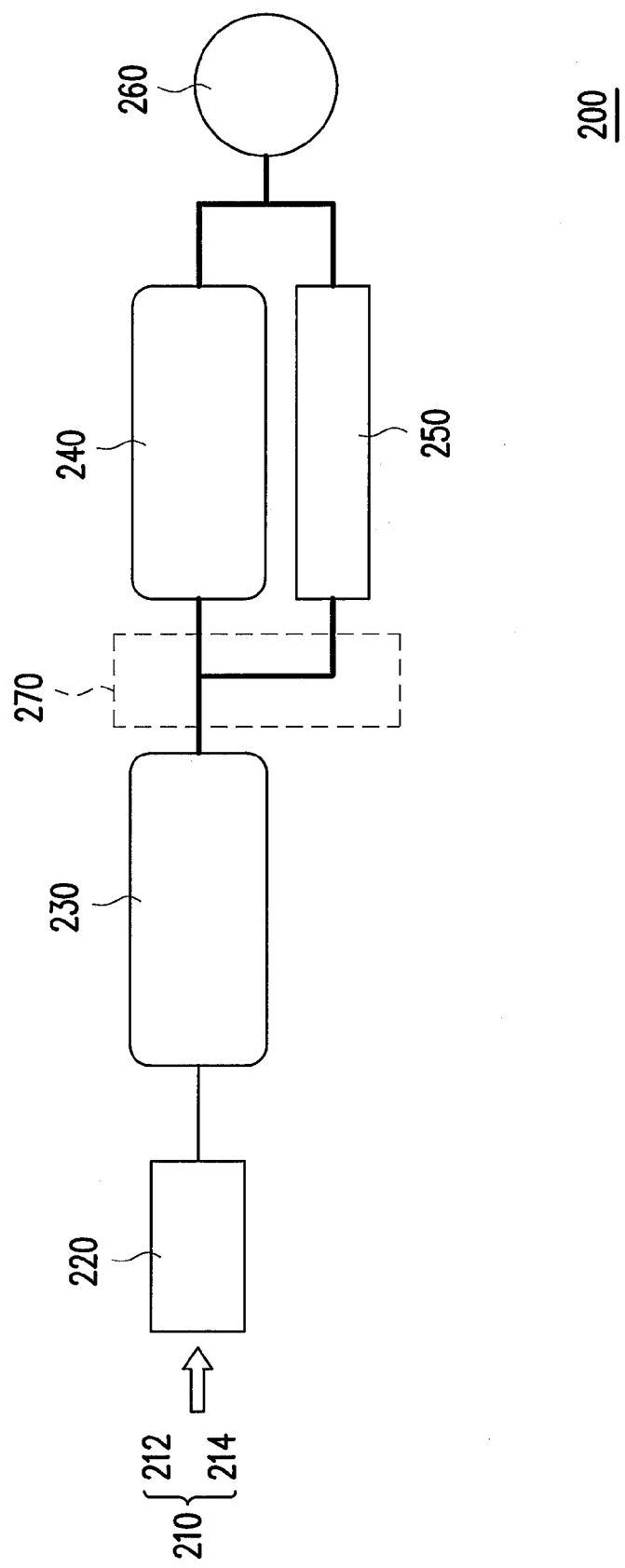
FIG. 1 is a schematic view of a fluid separation apparatus according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

In the present invention, a multi-channel valve is used to connect a first separation column and a second separation column for separating fluids with different properties respectively in series. Furthermore, by appropriately setting the multi-channel valve to different modes at different time sequence, a flow-through status and a closed status of communication among the first separation column, the second separation column, a bypass line, and a single detector are controlled, such that each component with different physical properties in a mixed fluid is detected by the same detector. In this manner, through a fluid separation apparatus and a fluid separation method according to the present invention, not only a simple separating and analyzing manner is provided, but also the mixed fluid can be highly efficiently separated or analyzed by appropriately setting a guide multi-channel valve to different modes. Thus, when the fluid separation apparatus and the fluid separation method according to the present invention are applied to the industry, not only a manufacturing cost and an occupied space are reduced, but also the fluid separation apparatus and the fluid separation method that are simple and convenient and capable of highly efficiently separating the mixed fluid are provided for users. Definitely, the fluid separation apparatus and the fluid separation method may also be used as a fluid chromatography apparatus and a fluid chromatography method in terms of the practical applications, and the present invention is not limited to a certain application range. Operating mechanisms of the fluid separation apparatus and the fluid separation method according to the present invention are exemplified as follows, which are not intended to limit the present invention.

First Embodiment

FIG. 1 is a schematic view of a fluid separation apparatus according to an embodiment of the present invention. A fluid separation apparatus 200 is suitable for separating a mixed fluid 210 with different properties, in which the properties refer to physical properties herein. Definitely, the mixed fluid 210 may be a mixed gas or a mixed liquid, which is not limited in the present invention. The mixed fluid 210 at least includes a first fluid 212 and a second fluid 214. In this embodiment, the first fluid 212 and the second fluid 214 are a non-polar fluid and a polar fluid respectively. Referring to FIG. 1, the fluid separation apparatus 200 mainly includes a sampling entrance 220, a first separation column 230, a second separation column 240, a bypass line 250, a detector 260, and a guide multi-channel valve 270. In particular, the first separation column and the second separation column may employ chromatography columns.

Referring to FIG. 1, a mixed fluid flows into the fluid separation apparatus 200 via the sampling entrance 220. An entrance side of the first separation column 230 is connected to the sampling entrance 220, the second separation column 240 is connected to an exit side of the first separation column 230 in series, and the bypass line 250 is connected to the second separation column 240 in parallel and is connected to the first separation column 230 in series. The first separation column 230 and the second separation column 240 are respectively used for separating the first fluid 212 and the second fluid 214. In other words, in this embodiment, the first separation column 230 and the second separation column 240 are, for example, a chromatography column for separating the polar fluid and a chromatography column for separating the non-polar fluid respectively.

Referring to FIG. 1, the detector 260 is connected to the second separation column 240 and the bypass line 250. In other words, the exit side of the first separation column 230 is connected to an entrance side of the second separation column 240 and an entrance side of the bypass line 250, and an exit side of the second separation column 240 and an exit side of the bypass line 250 are connected to the detector 260, in which the detector 260 is used to detect the first fluid 212 and the second fluid 214 after they are separated. The guide multi-channel valve 270 is connected to the exit side of the first separation column 230, the entrance side of the second separation column 240, the entrance side of the bypass line 250, and the detector 260. It should be noted that, the guide multi-channel valve 270 has different modes, for controlling communication between the first separation column 230 and the second separation column 240, communication between the first separation column 230 and the bypass line 250, communication between the second separation column 240 and the detector 260, and communication between the bypass line 250 and the detector 260 respectively in a flow-through status or in a closed status.

Figure 2A:
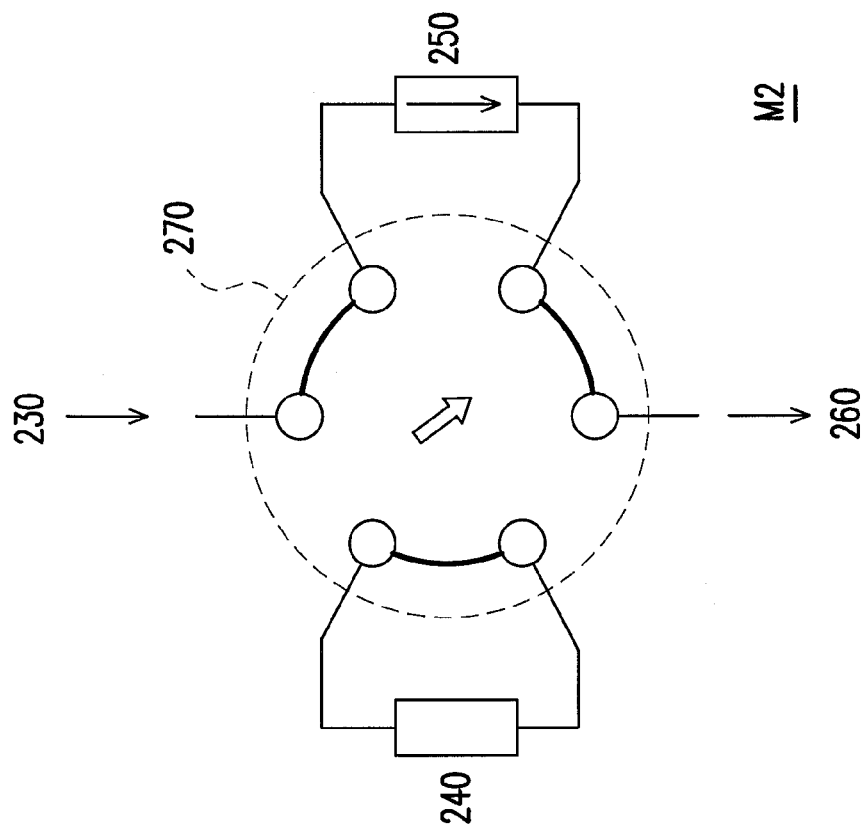
FIGS. 2A and 2B are schematic views of internal pipelines according to an embodiment of the present invention when a guide multi-channel valve is in different modes respectively.
Figure 2B:
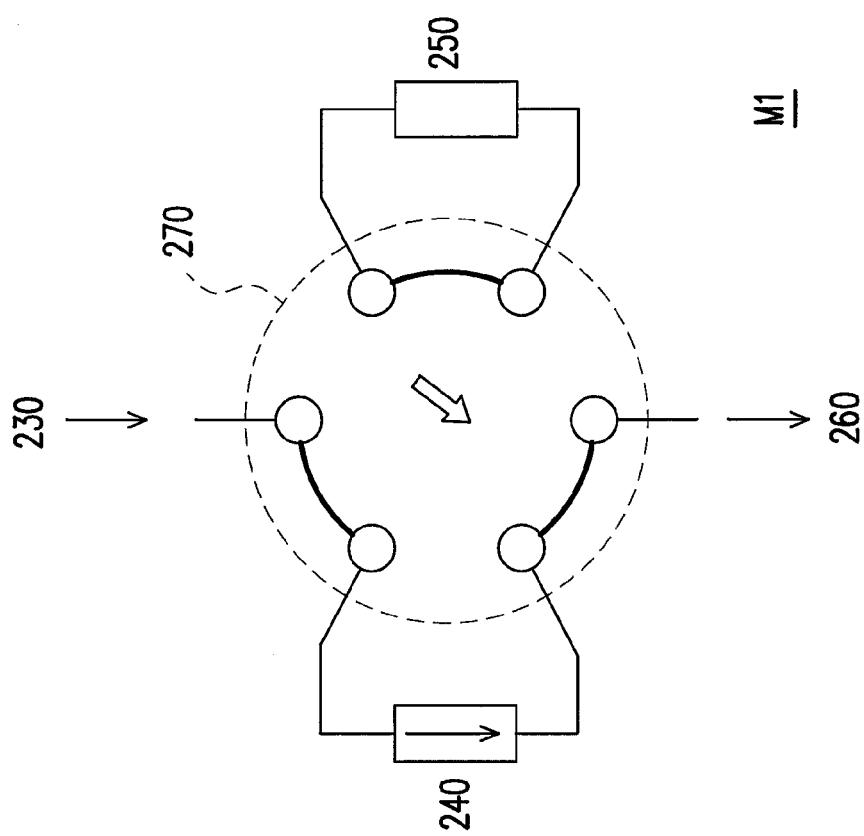

FIGS. 2A and 2B are schematic views of internal pipelines according to an embodiment of the present invention when a guide multi-channel valve is in different modes respectively, in which the guide multi-channel valve 270 of FIG. 2A is in a first mode M1, and the guide multi-channel valve 270 of FIG. 2B is in a second mode M2. Referring to FIG. 2A, when the guide multi-channel valve 270 is in the first mode M1, the mixed fluid 210 flows in a flowing direction from the first separation column 230 to the detector 260 through the second separation column 240. In other words, when the guide multi-channel valve 270 is in the first mode M1, the second fluid 214 (as shown in FIG. 1) may be delivered to the second separation column 240, and then the second fluid 214 (as shown in FIG. 1) after being separated by the second separation column 240 is further detected by the detector 260 through the guide multi-channel valve 270 in the first mode M1. On the other aspect, referring to FIG. 2B, when the guide multi-channel valve 270 is in the second mode M2, the mixed fluid 210 flows in a flowing direction from the first separation column 230 to the detector 260 through the bypass line 250. In other words, when the guide multi-channel valve 270 is in the second mode M2, the first fluid 212 (as shown in FIG. 1) after being separated by the first separation column 230 is detected by the detector 260 through the guide multi-channel valve 270 in the second mode M2. Meanwhile, when the guide multi-channel valve 270 is in the second mode M2, the second fluid 214 (as shown in FIG. 1) flowing to the second separation column 240 is trapped within the second separation column 240 for performing a separation procedure. For ease of description, the schematic views of external pipelines between the guide multi-channel valve 270 and the first separation column 230, the second separation column 240, the bypass line 250, and the detector 260 when the guide multi-channel valve 270 is in different modes are shown respectively.

FIGS. 3A and 3B are schematic views of external pipelines respectively corresponding to connection relations between the guide multi-channel valve and other members of FIGS. 2A and 2B. In order to simplify the drawings, only the pipelines in a flow-through status are shown, and the pipelines in a closed status are not shown.

Referring to FIG. 3A, when the guide multi-channel valve 270 is in the first mode M1, communication between the first separation column 230 and the bypass line 250 is, for example, in a closed status, communication between the first separation column 230 and the second separation column 240 is, for example, in a flow-through status, and communication between the second separation column 240 and the detector 260 is in the flow-through status, and the bypass line 250 is, for example, in a loop closed status, such that components in the first separation column 230 may flow to the second separation column 240 and the detector 26 through the guide multi-channel valve 270 in the first mode M1.

On the other aspect, referring to FIG. 3B, when the guide multi-channel valve 270 is in the second mode M2, communication between the first separation column 230 and the second separation column 240 is, for example, in a closed status, communication between the first separation column 230 and the bypass line 250 is, for example, in a flow-through status, and communication between the bypass line 250 and the detector 260 is, for example, in a flow-through status, and the second separation column 240 is, for example, in a loop closed status, such that components of the first fluid 212 in the first separation column 230 may prevent from flowing to the second separation column 240 to damage the second separation column 240 when the guide multi-channel valve 270 is in the second mode M2. Furthermore, a user may timely make the second fluid stay within the second separation column 240 according to the actual demands through the guide multi-channel valve 270 in the second mode M2. Therefore, in the fluid separation apparatus according to the present invention, the guide multi-channel valve 270 is timely switched between the first mode M1 and the second mode M2, such that each component in the mixed fluid can be highly efficiently separated completely by using a single detector, and a part of the components of the mixed fluid can be prevented from damaging the second separation column. In the conventional gas separation technique, a detector must be respectively added after a separation column for separating the polar fluid and a separation column for separating the non-polar fluid. In the present invention, not only the occupied space and the manufacturing cost of the apparatus are saved, but also the fluid separation apparatus has economic benefits. On the other aspect, as for a mixed fluid that is hard to be separated, the fluid separation apparatus according to the present invention can effectively separate components with similar physical properties. For example, the gases belonging to the polar gas and the gases belonging to the non-polar gas may be respectively separated by using the separation column for separating the polar gas and the separation column for separating the non-polar gas, and may be detected by the same detector.

Figure 4:
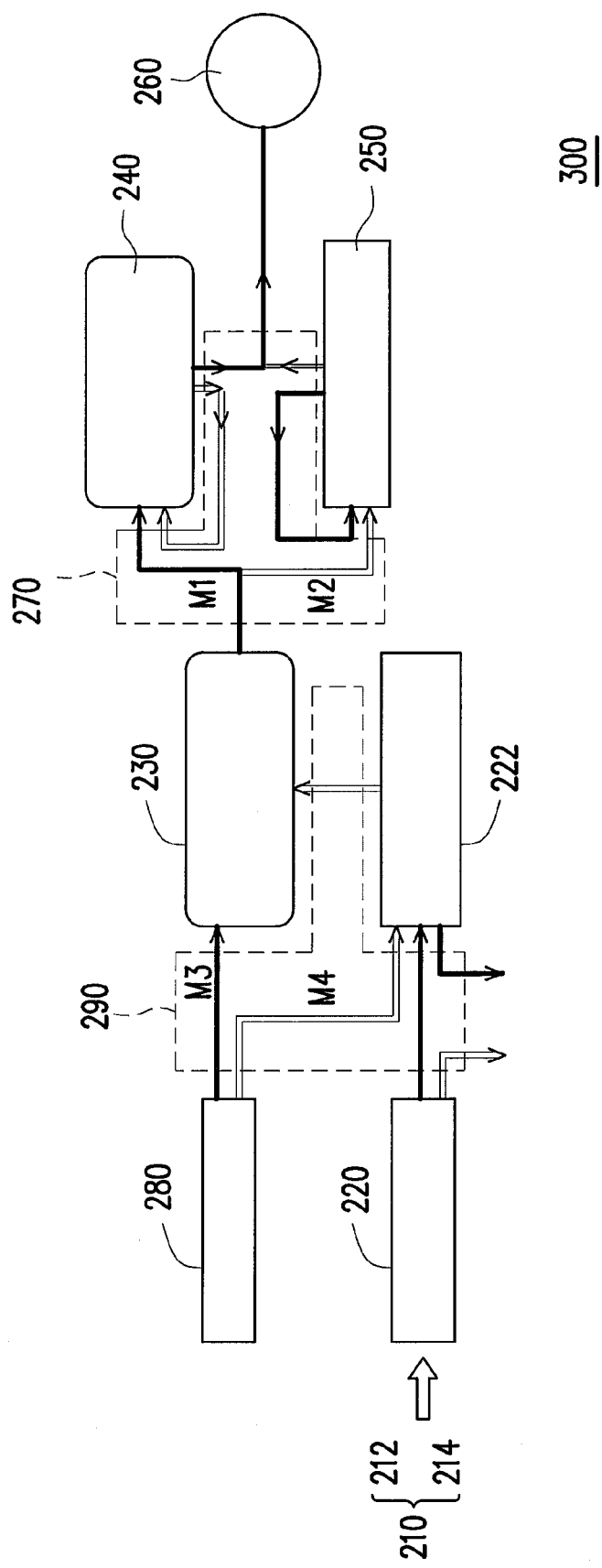
FIG. 4 is a schematic view of a fluid separation apparatus according to another embodiment of the present invention.

FIG. 4 is a schematic view of a fluid separation apparatus according to another embodiment of the present invention. Referring to FIG. 4, a fluid separation apparatus 300 in this embodiment is similar to the fluid separation apparatus 200 of the above embodiment, except that the fluid separation apparatus 300 in this embodiment further includes a sampling loop 222 and a carrier gas 280. The sampling loop 222 is connected between the sampling entrance 220 and the first separation column 230, and the mixed fluid 210 is delivered in a direction from the sampling entrance 220 to the detector 260 through the carrier gas 280. In addition, in this embodiment, the fluid separation apparatus 300 further includes a sampling multi-channel valve 290 disposed between the first separation column 230 and the sampling entrance 220. The sampling multi-channel valve 290 is similar to the guide multi-channel valve 270, and has a plurality of contacts therein. Different operating modes of the sampling multi-channel valve 290 are set through connection relations among the contacts, so as to control a flow-through status and a closed status between the sampling loop 222 and the first separation column 230, between the sampling entrance 220 and the sampling loop 222, between the carrier gas 280 and the first separation column 230, and between the carrier gas 280 and the sampling loop 222.

Figure 5B:
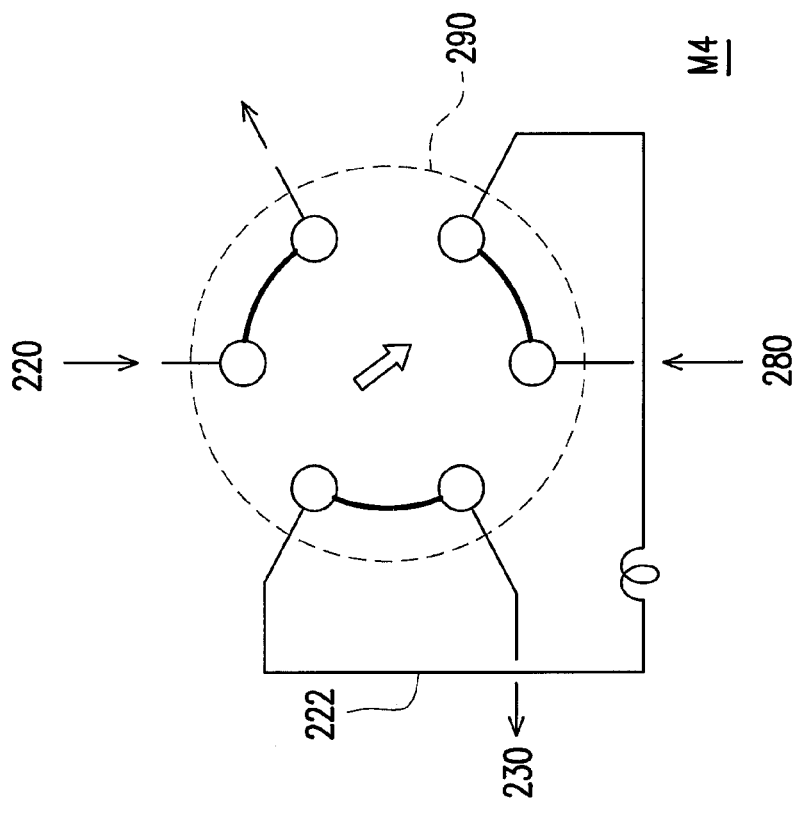
FIGS. 5A and 5B are schematic views of internal pipelines according to an embodiment of the present invention when a sampling multi-channel valve is in different modes respectively.
Figure 5A:
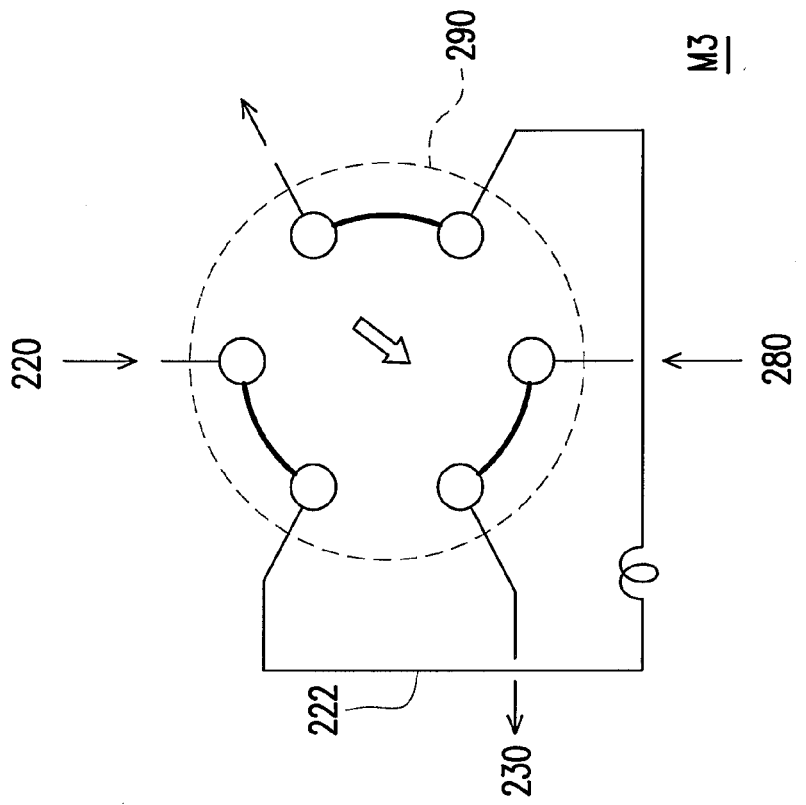

Particularly, FIGS. 5A and 5B are schematic views of internal pipelines according to an embodiment of the present invention when a sampling multi-channel valve is in different modes respectively, in which FIG. 5A is a schematic view of internal pipelines when the sampling multi-channel valve is in a preset sampling mode, and FIG. 5B is a schematic view of internal pipelines when the sampling multi-channel valve is in a sample inlet mode. Referring to FIG. 5A, when the sampling multi-channel valve 290 is in a preset sampling mode M3, the mixed fluid 210 flows in a flowing direction from the sampling entrance 220 to the sampling loop 222, and the mixed fluid 210 is filled in the sampling loop 222. Next, referring to FIG. 5B, when the sampling multi-channel valve 290 is in a sample inlet mode M4, the mixed fluid filled in the sampling loop 222 is delivered to the first separation column 230 through the carrier gas 280.

In order to describe the embodiment clearly, schematic views of external pipelines between the sampling multi-channel valve 290 and the sampling entrance 220, the sampling loop 222, the carrier gas 280, the first separation column 230, and the detector 260 when the sampling multi-channel valve 290 is in different modes are respectively shown and are further described below in detail. To simplify the drawings, only the pipelines in a flow-through status are shown, and the pipelines in a closed status are not shown.

FIGS. 6A and 6B are schematic views of external pipelines respectively corresponding to connection relations between the sampling multi-channel valve and other members of FIGS. 5A and 5B. Referring to FIG. 6A, when the sampling multi-channel valve 290 is in the preset sampling mode M3, communication between the sampling entrance 220 and the sampling loop 222 is in a flow-through status, communication between the sampling entrance 220 and the first separation column 230 is in a closed status, and the carrier gas 280 flows in a direction from an entrance of the first separation column 230 to the detector 260. On the other aspect, referring to FIG. 6B, when the sampling multi-channel valve 290 is in the sample inlet mode M4, communication between the sampling entrance 220 and the sampling loop 222 is in a closed status, communication between the carrier gas 280 and the sampling loop 222 is in a flow-through status, and communication between the sampling loop 222 and the first separation column 230 is in a flow-through status, and the carrier gas 280 flows in a direction from the sampling loop 222 to the first separation column 230.

Second Embodiment

In order to make the technical content of the present invention more comprehensible, a fluid separation method according to a second embodiment of the present invention is described below with reference to FIGS. 7A to 7C, in which a gas including $H_2$, $CO_2$, and $H_2O$ is, for example, used as a mixed fluid 210 to be separated.

Figure 7A:
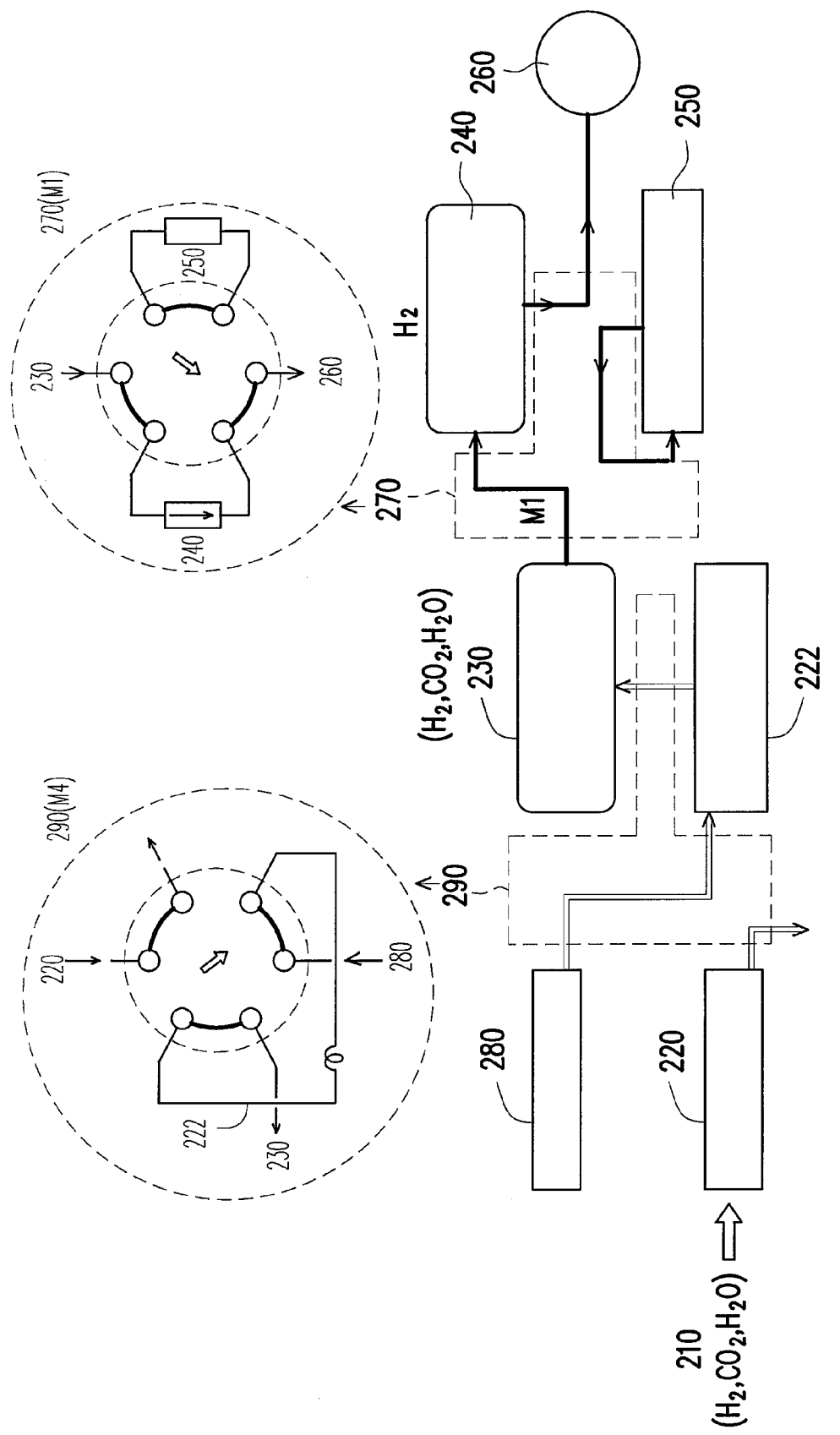
FIGS. 7A to 7C show a processing flow of a fluid separation method according to a second embodiment of the present invention.
Figure 7B:
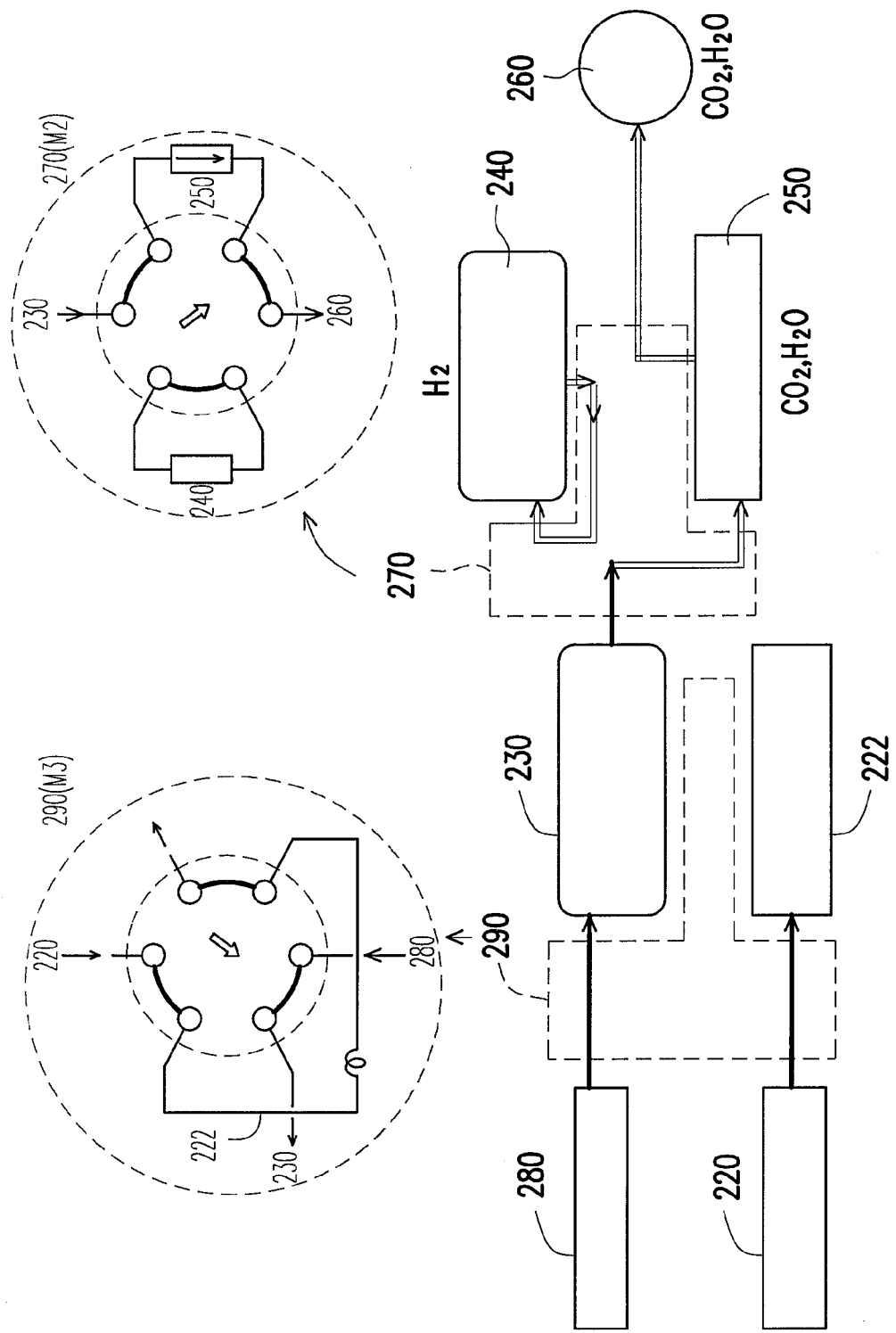
Figure 7C:
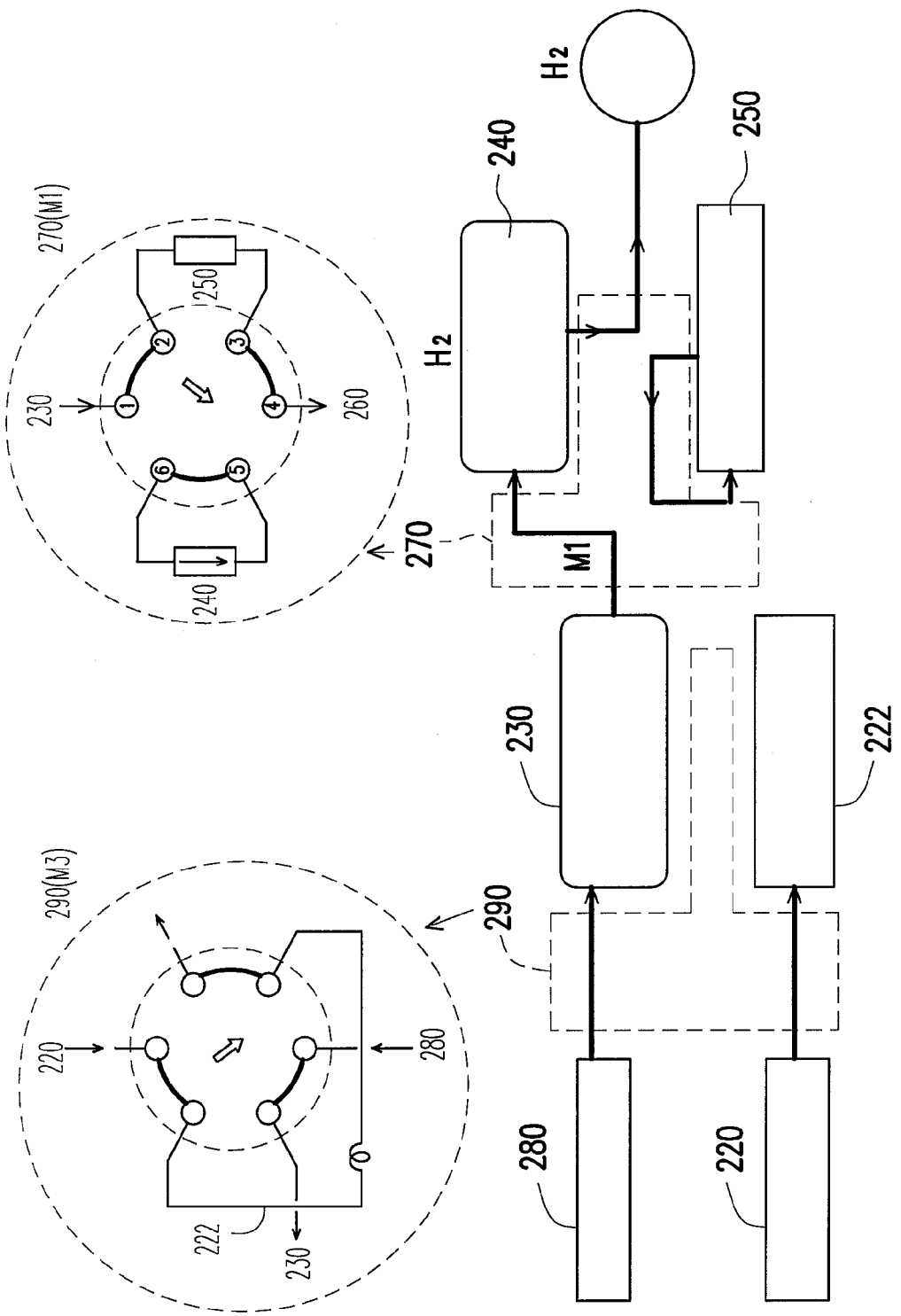

FIGS. 7A to 7C show a processing flow of a fluid separation method according to a second embodiment of the present invention. Referring to FIG. 7A, first, a mixed fluid 210 with different properties is provided, and the mixed fluid 210 includes components of $H_2$, $CO_2$, and $H_2O$, in which the mixed fluid 210 at least includes a first fluid $CO_2$ and $H_2O$ belonging to a polar fluid and a second fluid $H_2$ belonging to a non-polar fluid. Next, the mixed fluid $H_2$, $CO_2$, and $H_2O$ is delivered to a first separation column 230 via a sampling entrance 220, and the process of providing the mixed fluid 210 to the first separation column 230 via the sampling entrance 220 can be obtained with reference to the descriptions of FIGS. 5A-5B and FIGS. 6A-6B in the first embodiment, and the descriptions thereof are omitted here.

Referring to FIG. 7A, a guide multi-channel valve 270 is set to a first mode M1. When the guide multi-channel valve 270 is set to the first mode M1, communication between the first separation column 230 and a bypass line 250 is in a closed status, communication between the first separation column 230 and a second separation column 240 is in a flow-through status, and communication between the second separation column 240 and the detector 260 is in a flow-through status, and the bypass line 250 is in a loop closed status. Therefore, the first fluid $CO_2$ and $H_2O$ as the polar fluid in the mixed fluid 210 performs a separation procedure in the first separation column 230. Furthermore, in this embodiment, no reaction occurs between the first separation column 230 and the second fluid $H_2$, such that the second fluid $H_2$ in the mixed fluid 210 directly passes through the first separation column 230, and flows to the second separation column 240 through the guide multi-channel valve 270 in the first mode M1, and the second fluid 214 performs a separation procedure in the second separation column 240.

Next, referring to FIG. 7B, the guide multi-channel valve 270 is switched to a second mode M2. As described above, when the guide multi-channel valve 270 is in the second mode M2, communication between the first separation column 230 and the second separation column 240 is in a closed status, communication between the first separation column 230 and the bypass line 250 is in a flow-through status, and communication between the bypass line 250 and the detector 260 is in a flow-through status, and the second separation column 240 is in a loop closed status. Therefore, referring to FIG. 7B, the second fluid $H_2$ is trapped within the second separation column 240, and the first fluid $CO_2$ and $H_2O$ separated by the first separation column 230 flows to the bypass line 250 through the guide multi-channel valve 270 in the second mode M2, and then is detected by the detector 260. Furthermore, it should be noted that, in this stage, a sampling multi-channel valve 290 may return to a preset sampling mode M3 from a sample inlet mode M4. In other words, the sampling entrance 220 and the sampling loop 222 are in a flow-through status, the sampling entrance 220 and the first separation column 230 are in a closed status, and the carrier gas 280 flows in a direction from an entrance of the first separation column 230 to the detector 260.

Then, referring to FIG. 7C, the guide multi-channel valve 270 is switched to the first mode M1, such that the second fluid $H_2$ trapped within the second separation column 240 and separated by the second separation column 240 is delivered to the same detector 260 through the guide multi-channel valve 270 for being detected. It should be noted that, in this step, the user may select to switch the guide multi-channel valve 270 from the second mode M2 to the first mode M1 at any time in consideration of the design, manufacturing process, or other demands. In this manner, the user may easily control a time difference for detecting the second fluid 214 and the first fluid 212 by the detector 260. Similarly, at this time, the sampling multi-channel valve 290 may be set to the preset sampling mode M3, but it is not limited here, in which the descriptions about the sampling multi-channel valve 290 when being set to the preset sampling mode M3 may be obtained with reference to the above descriptions, so the descriptions thereof are omitted here.

Figure 8A:
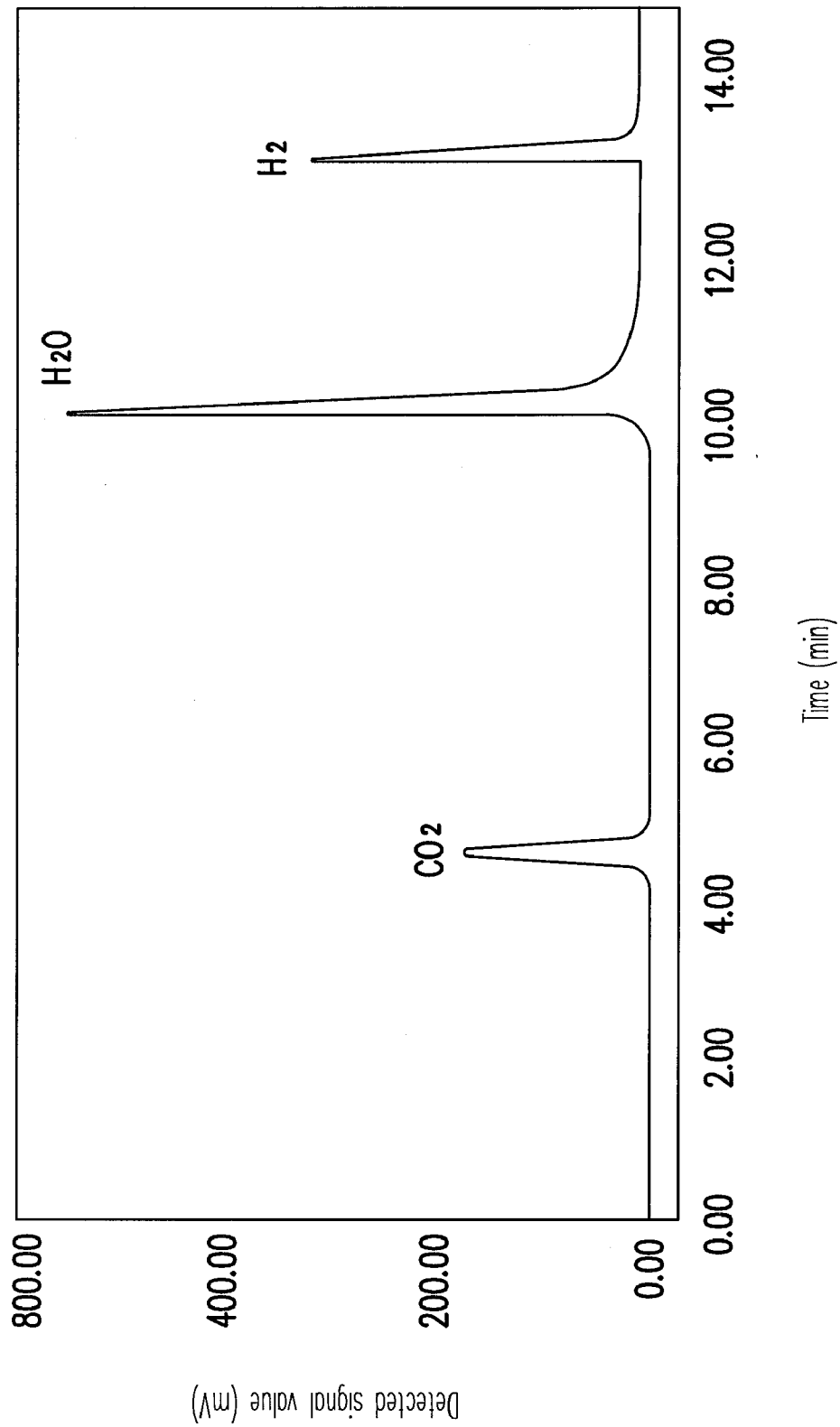
FIGS. 8A and 8B are schematic views of chromatogram tested by using the fluid separation method of FIGS. 7A to 7C.
Figure 8B:
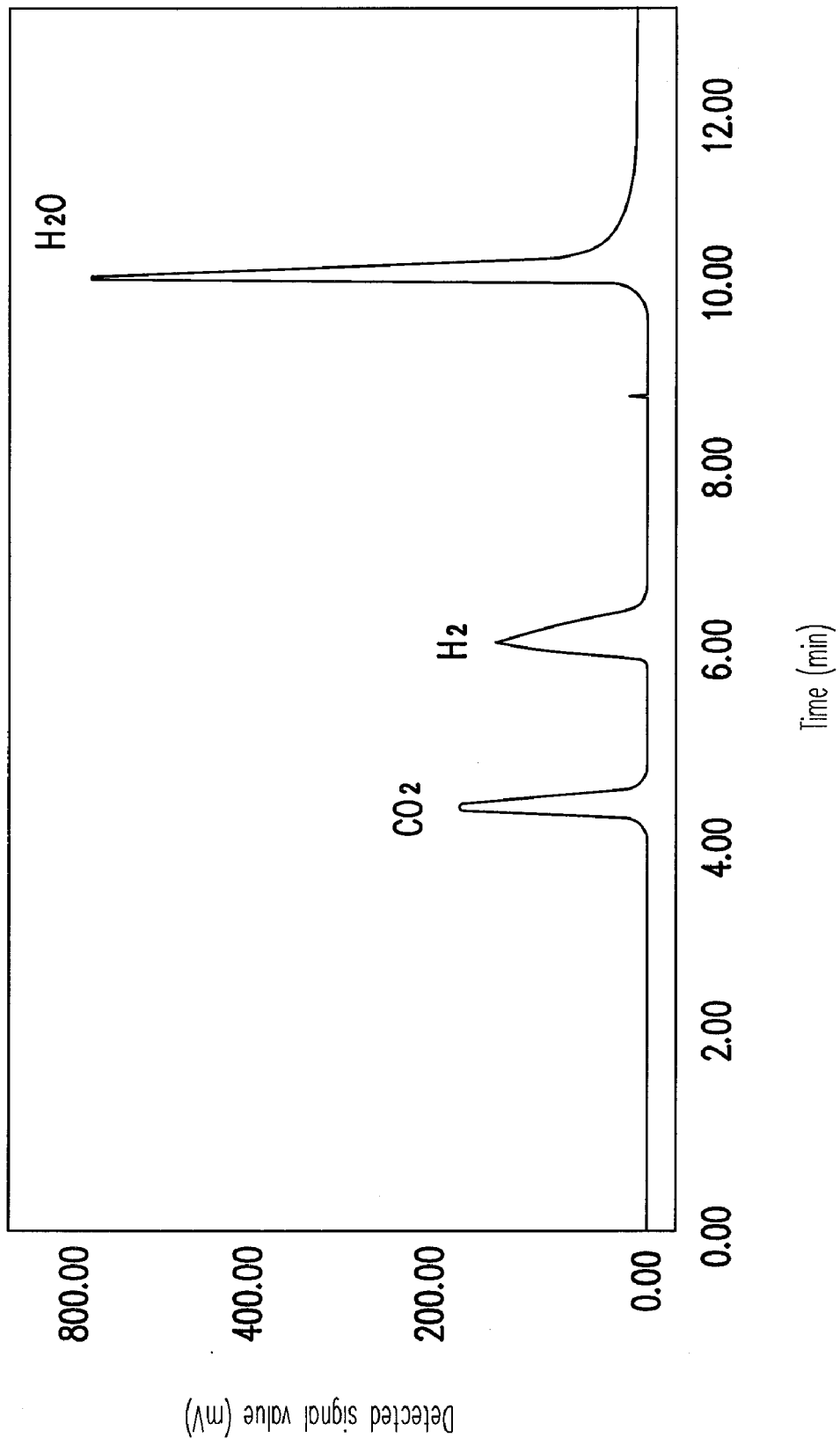

FIGS. 8A and 8B are schematic views of chromatogram tested by using the fluid separation method of FIGS. 7A to 7C. Referring to FIGS. 8A and 8B, a detecting sequence of each component in the mixed fluid 210 may be changed by using the fluid separation method according to the present invention. For example, based on thermodynamics and dynamics theories, in this embodiment, an occurrence sequence of the mixed fluid $H_2$, $CO_2$, and $H_2O$ on the chromatogram is first $H_2$, then $CO_2$, and finally $H_2O$. However, the fluid separation method according to this embodiment can overcome the limits of thermodynamics and dynamics. Referring to FIG. 8A, an occurrence time point of $H_2$ on the chromatogram is later than that of $CO_2$ and $H_2O$. Definitely, referring to FIG. 8B, through the fluid separation method of this embodiment, the occurrence time point of $H_2$ on the chromatogram may fall between that of $CO_2$ and $H_2O$, and the present invention is not limited here. Therefore, the fluid separation method of this embodiment can provide a brand new manner for performing column chromatography to cater to different demands of the users. Thus, an application freedom degree is improved, and the guide multi-channel valve can effectively prevent the separation column for separating the non-polar gas from being damaged due to being blocked by ionic bonds generated by the polar gas. In other words, the first fluid does not flow through the second separation column. Particularly, in the fluid separation method of this embodiment, each component in the mixed fluid is highly efficiently separated by only using a single detector, and the polar fluid and the non-polar fluid are further detected.

Third Embodiment

In order to make the technical content of the present invention more comprehensible, a fluid separation method according to a third embodiment of the present invention is described below with reference to FIGS. 9A to 9D, in which a gas of a group consisting of $H_2$, $O_2$, $N_2$, $CH_4$, CO, $CO_2$, $H_2O$, $CH_3OH$, and $C_2H_5OH$ is, for example, used as a mixed fluid 210 to be separated.

FIGS. 9A to 9D show a processing flow of a fluid separation method according to a third embodiment of the present invention. For ease of description, in this embodiment, those parts in this embodiment similar to the processing flow as shown in FIGS. 7A to 7C are not described.

Figure 9A:
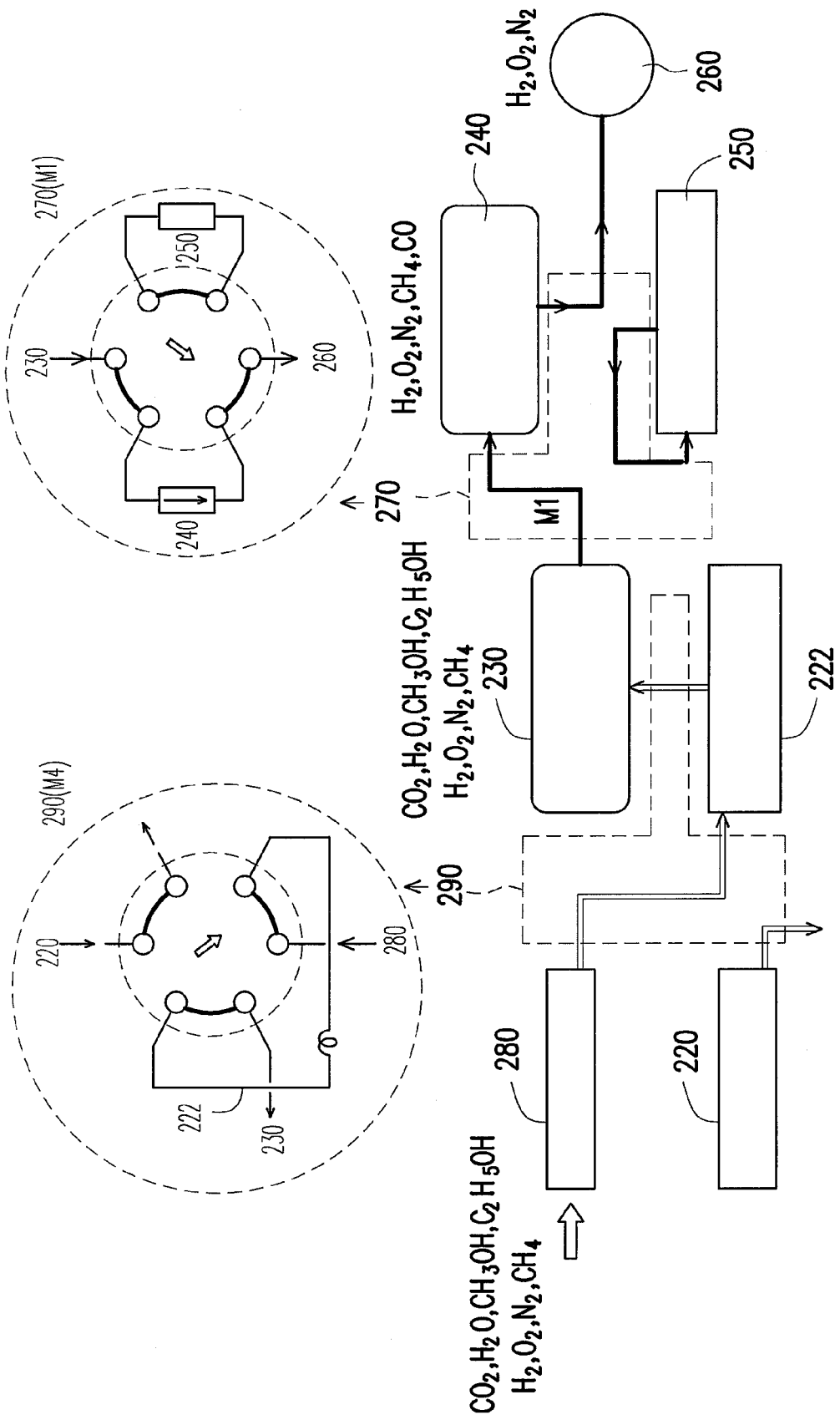
FIGS. 9A to 9D show a processing flow of a fluid separation method according to a third embodiment of the present invention.

Briefly, in the flow of FIG. 9A, a sampling multi-channel valve 290 is switched from a preset sampling mode M3 to a sample inlet mode M4, such that the mixed fluid $H_2$, $O_2$, $N_2$, $CH_4$, CO, $CO_2$, $H_2O$, $CH_3OH$, and $C_2H_5OH$ including both the polar gas and the non-polar gas is delivered to a first separation column 230 via a sampling entrance 220, among which the group of $CO_2$, $H_2O$, $CH_3OH$, and $C_2H_5OH$ serving as a first fluid 212 is the polar gas, and the group of $H_2$, $O_2$, $N_2$, $CH_4$, and CO serving as a second fluid 214 is the non-polar gas.

Referring to FIG. 9A, the first fluid $CO_2$, $H_2O$, $CH_3OH$, and $C_2H_5OH$ performs a separation procedure in the first separation column 230, and the second fluid $H_2$, $O_2$, $N_2$, $CH_4$, and CO enters a second separation column 240 via a guide multi-channel valve 270 in a first mode M1 to perform a separation procedure. Furthermore, a first part $H_2$, $O_2$, and $N_2$ of the second fluid is earlier separated in the second separation column 240, and thus, in this step, the first part $H_2$, $O_2$, and $N_2$ of the second fluid 214 flows to the detector 260 through the guide multi-channel valve 270 in the first mode M1 for being firstly detected. In one situation, when $CH_4$ and CO do not completely flow out of the second separation column 240, if a part of $CO_2$ flows from the first separation column 230 to the second separation column 240, this part of $CO_2$ would generate ionic bonds with particles filled in the second separation column 240 and block the second separation column 240, and in this case, the technique of the second embodiment can overcome such a problem, which exhibits the necessity of the technique.

Figure 9B:
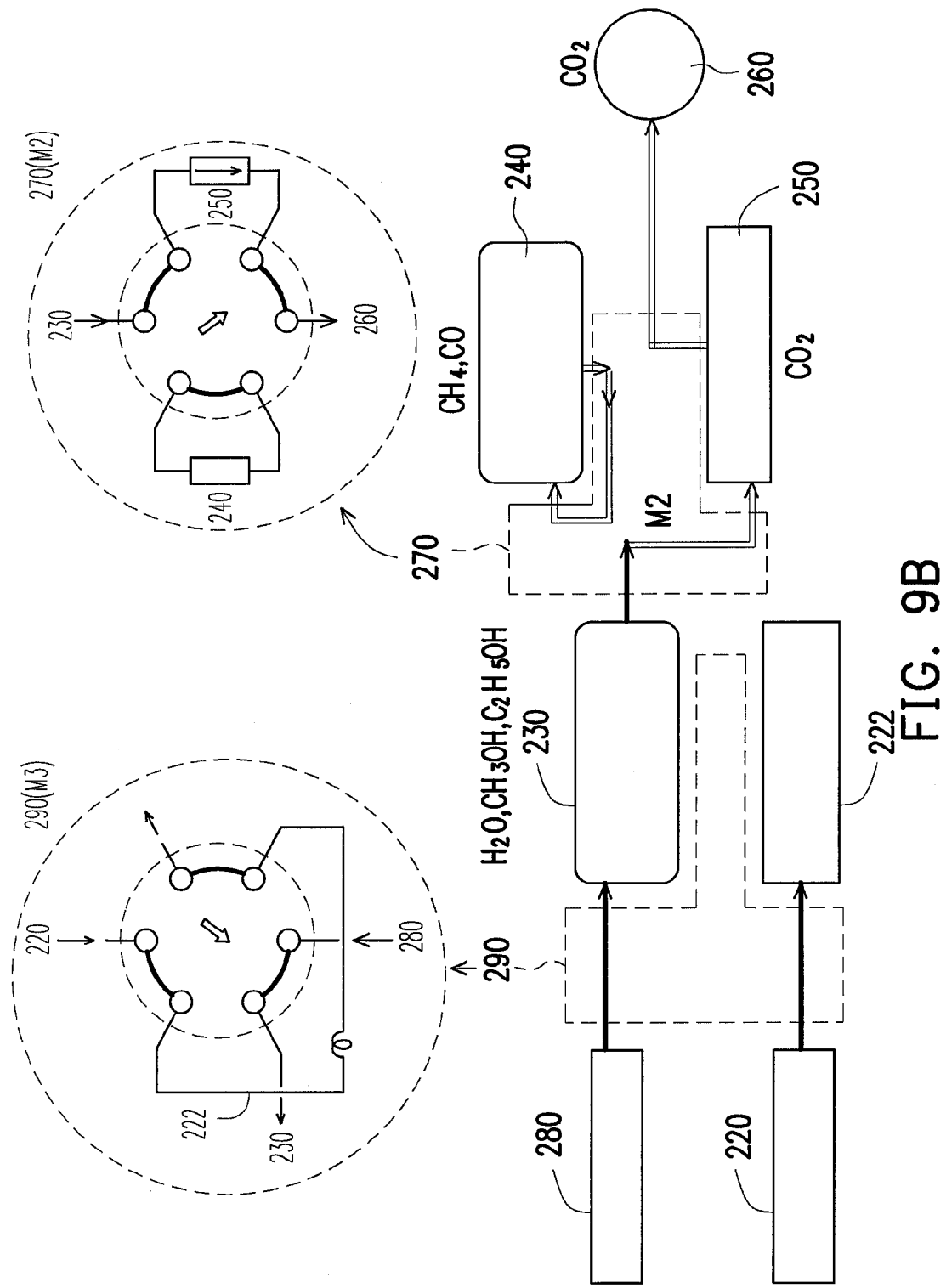

Referring to FIG. 9B, a first part of the first fluid, i.e. $CO_2$, in the first separation column 230 has a much higher separation speed. Thus, before the first part $CO_2$ that is separated earlier by the first separation column 230 enters the second separation column 240, the guide multi-channel valve 270 is switched to the second mode M2, such that the first part $CO_2$ of the first fluid that is separated earlier by the first separation column 230 is detected by the detector 260 through the guide multi-channel valve 270 in the second mode M2. It should be noted that, at this time, a second part $CH_4$ and CO of the second fluid 214 is still left in the second separation column 240 for performing the separation procedure.

Figure 9C:
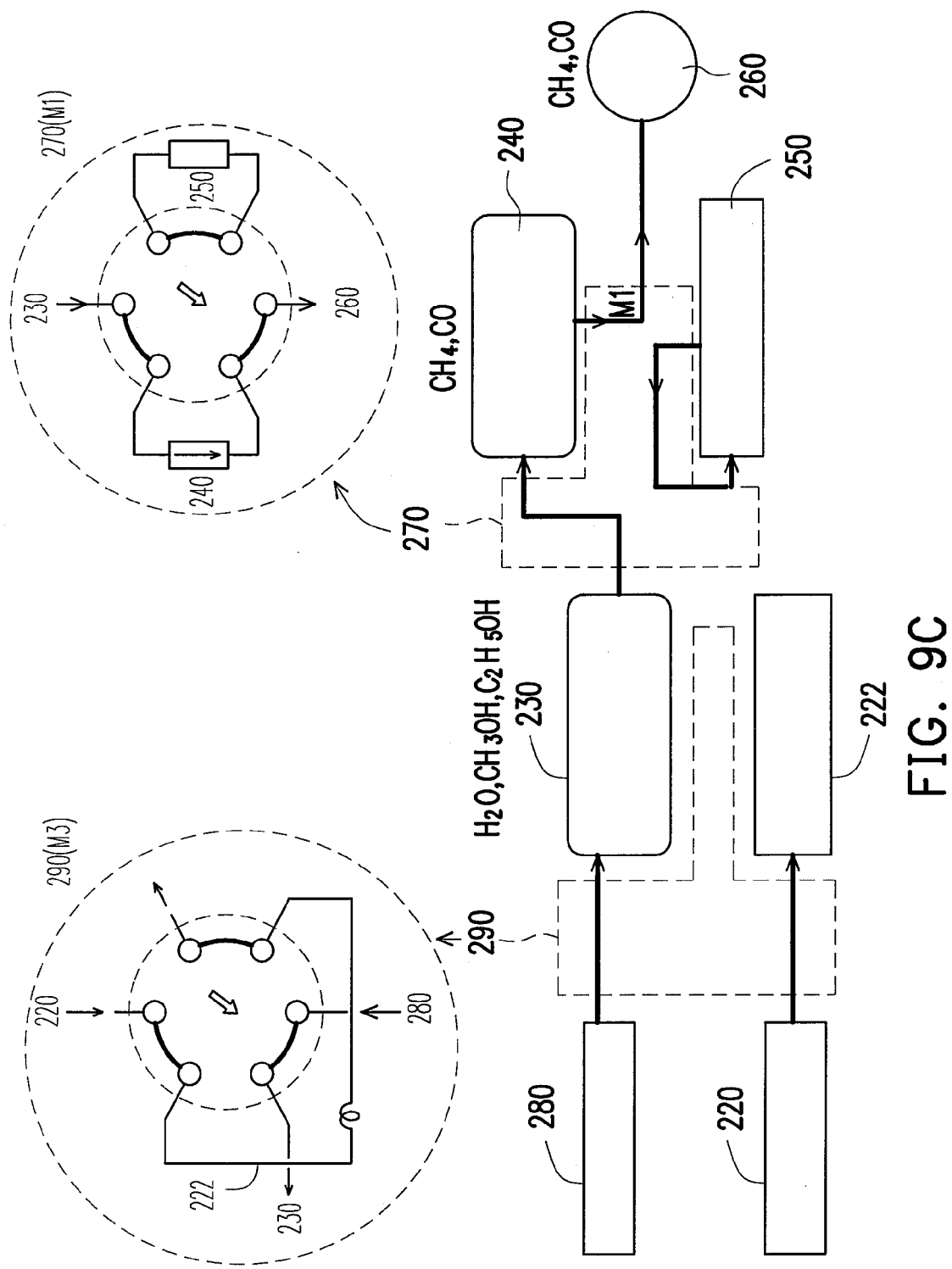

Then, referring to FIG. 9C, the guide multi-channel valve 270 is switched to the first mode M1, a second part $H_2O$, $CH_3OH$, and $C_2H_5OH$ of the first fluid 212 is still left in the first separation column 230 and performs a separation procedure, and the second part $CH_4$ and CO of the second fluid 214 left in the second separation column 240 in the above step and already separated by the second separation column 240 at this time is delivered to the same detector 260 through the guide multi-channel valve 270 in the first mode M1 for being detected. Furthermore, in order to further increase a flow rate difference between the first fluid 212 and the second fluid 214 to improve a fluid separation effect, a heating-up procedure is performed on the second part $CH_4$ and CO of the second fluid 214 left in the second separation column 240 in this step.

Figure 9D:
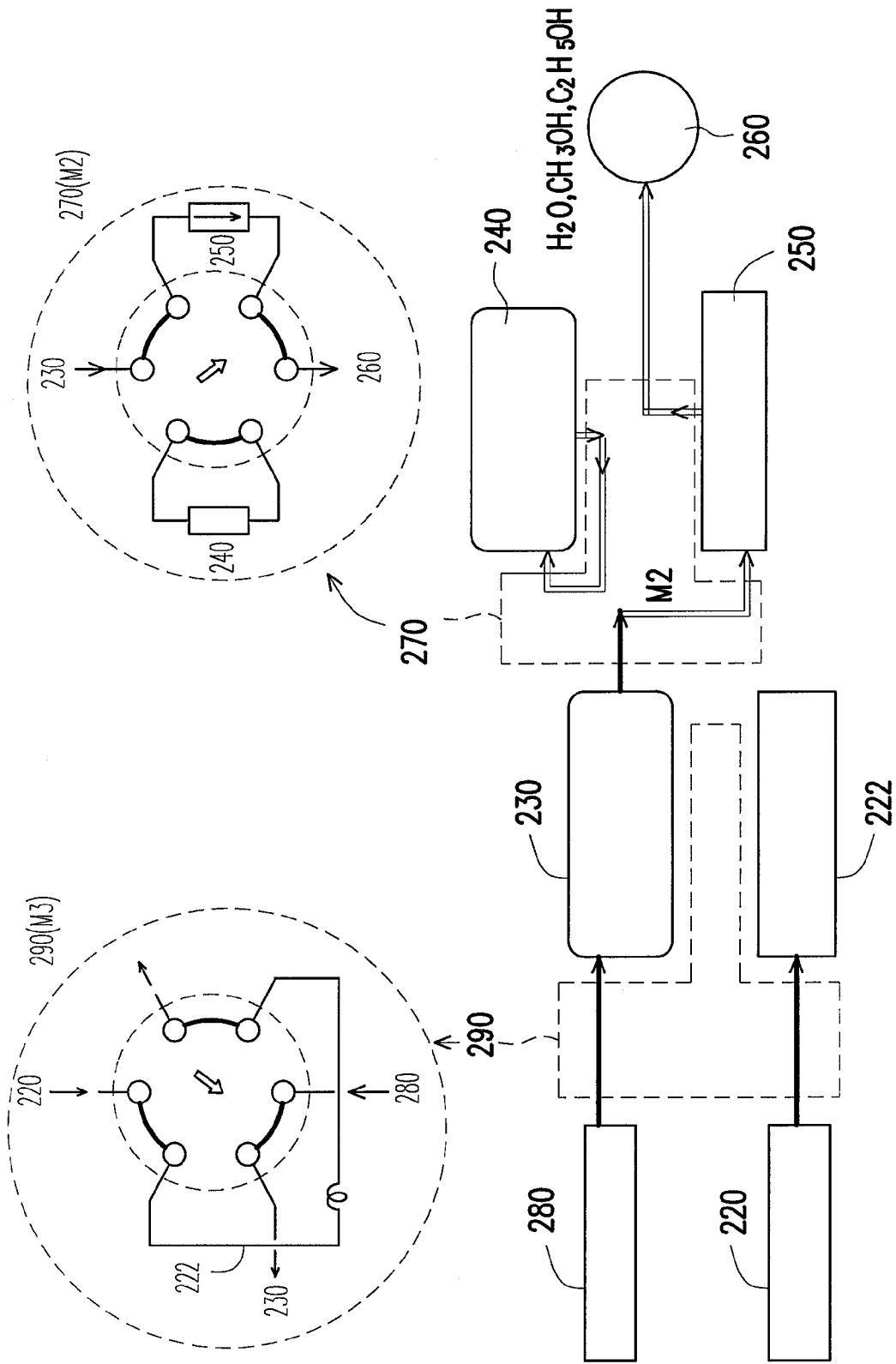

Next, referring to FIG. 9D, the guide multi-channel valve 270 is switched to the second mode M2, and the second part $H_2O$, $CH_3OH$, and $C_2H_5OH$ of the first fluid 212 left in the first separation column 230 and already separated by the first separation column 230 is delivered to the same detector 260 through the guide multi-channel valve 270 in the second mode M2 for being detected.

Figure 10:
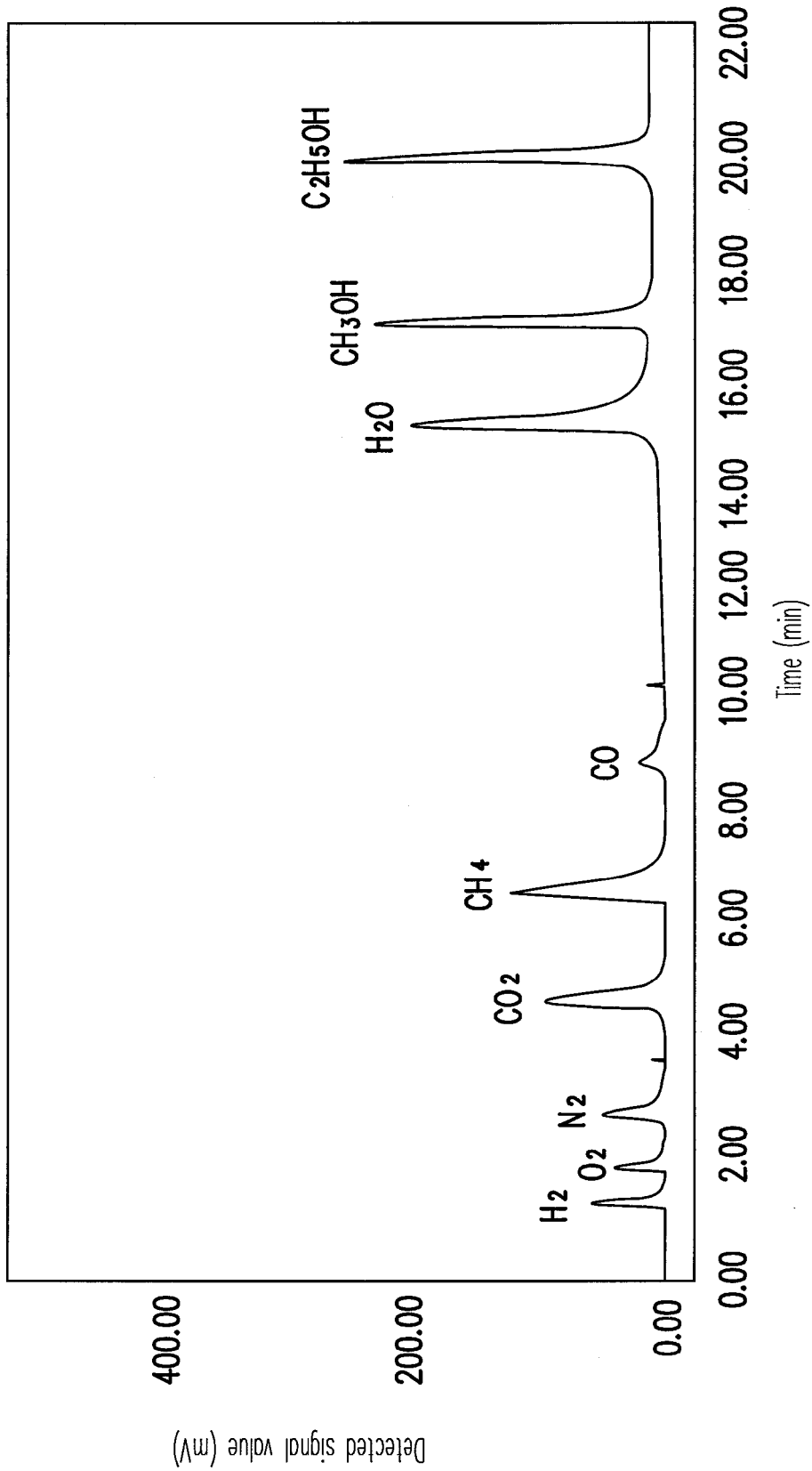
FIG. 10 is a schematic view of chromatogram tested by using the fluid separation method of FIGS. 9A to 9D.

FIG. 10 is a schematic view of chromatogram tested by using the fluid separation method of FIGS. 9A to 9D. Referring to FIG. 10, a complex fluid mixture may be highly efficiently separated by using the fluid separation method according to the present invention. Referring to FIG. 10, in the fluid separation method of this embodiment, the complex fluid mixture can be highly efficiently separated by only using a single detector 260. Therefore, in the fluid separation method of this embodiment, not only the space and the cost of the apparatus are saved, but also the complex fluid mixture is completely separated.

Figure 11B:
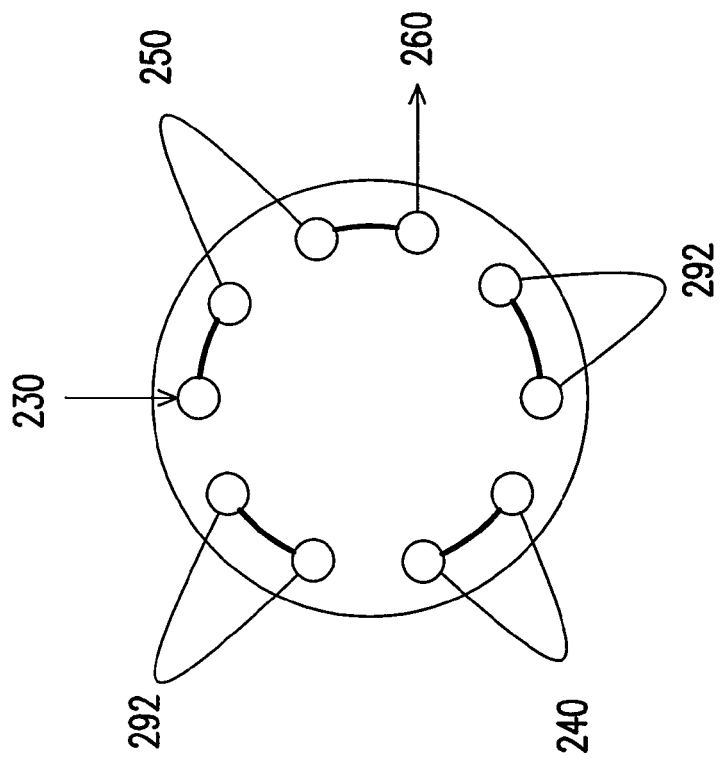
FIGS. 11A and 11B are schematic views of internal pipelines according to an embodiment of the present invention when another guide multi-channel valve is respectively in different modes.

In addition, in the above embodiments, a type of the guide multi-channel valve 270 is, for example, a six-port valve. It should be noted that, the guide multi-channel valve 270 according to the present invention may be other types, for example, in this embodiment, a guide multi-channel valve 370 may be, for example, a ten-port valve, and the ten-port valve also has the first mode M1 and the second mode M2 as described above. Particularly, FIGS. 11A and 11B are schematic views of internal pipelines according to an embodiment of the present invention when another guide multi-channel valve is respectively in different modes, in which the design of the guide multi-channel valve 370 of FIG. 11A may be obtained with reference to the first mode M1, and the design of the guide multi-channel valve 370 of FIG. 11B may be obtained with reference to the second mode M2.

Figure 11A:
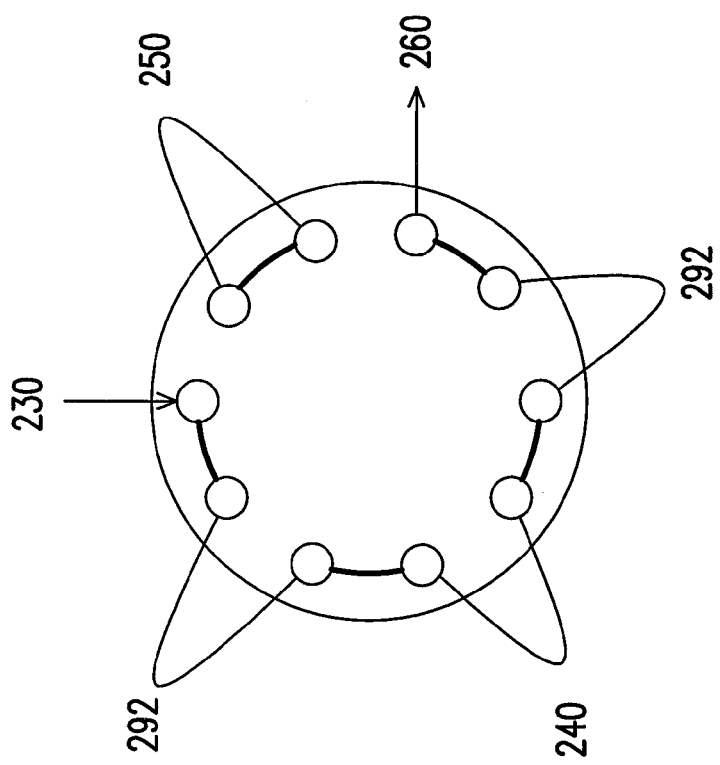

Briefly, referring to FIG. 11A, in this embodiment, when the guide multi-channel valve 370 is in the first mode M1, communication between the first separation column 230 and the bypass line 250 is in a closed status, communication between the first separation column 230 and the second separation column 240 is in a flow-through status through a hollow pipe or a third separation column 292, communication between the second separation column 240 and detector 260 is in a flow-through status through another hollow pipe or the third separation column 292, and the bypass line 250 is in a loop closed status. On the other aspect, referring to FIG. 11B, in this embodiment, when the guide multi-channel valve 370 is in the second mode M2, communication between the first separation column 230 and the second separation column 240 is in a closed status, communication between the first separation column 230 and the bypass line 250 is, for example, in a flow-through status, and communication between the bypass line 250 and the detector 260 is, for example, in a flow-through status, and the hollow pipes or the third separation column 292 and the second separation column 240 are, for example, respectively in a loop closed status. Therefore, the implementation of the guide multi-channel valve 270 is not limited in the present invention.

To sum up, the fluid separation method and the fluid separation apparatus according to the present invention at least have a part or all of the following advantages.

1. In the fluid separation method and the fluid separation apparatus according to the present invention, a guide multi-channel valve is appropriately arranged and different modes of the guide multi-channel valve are well designed. Thus, in an embodiment, an innovative pipeline design is used to prevent a separation column for separating the non-polar fluid from being blocked by ionic bonds generated by the polar fluid in the prior art, and no conventional condenser is disposed additionally, thereby saving the space and the cost. Furthermore, the fluid with different physical properties after being separated is detected by a single detector, thereby saving the cost and the space.

2. Through the design of a guide multi-channel valve and a bypass line, the limits of thermodynamics and dynamics may be overcome, such that the specific fluid appears on the chromatogram at the required time, and thus, a brand new manner for performing column chromatography is provided to cater to the different demands of the users.

3. As for a complex mixed fluid, in the fluid separation method and the fluid separation apparatus according to the present invention, various fluids in the mixed fluid can be highly efficiently separated completely, and each component in the mixed fluid can be efficiently separated.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fluid separation method, comprising:
providing a mixed fluid with different properties, wherein the mixed fluid at least comprises a first fluid and a second fluid, and the first fluid and the second fluid comprise different properties;
providing the mixed fluid via a sampling entrance, wherein the mixed fluid flows to a first separation column, the first fluid in the mixed fluid performs a separation procedure in the first separation column, the second fluid in the mixed fluid flows to a second separation column connected to the first separation column in series through a guide multi-channel valve, the second fluid performs a separation procedure in the second separation column, and at this time, the guide multi-channel valve is in a first mode;
switching the guide multi-channel valve to a second mode, such that the second fluid is trapped within the second separation column and the first fluid already separated by the first separation column flows through a bypass line connected to the first separation column in series via the guide multi-channel valve and is detected by a detector connected to the bypass line in series, wherein the bypass line is connected to the second separation column in parallel; and
switching the guide multi-channel valve to the first mode, such that the second fluid trapped within the second separation column and already separated by the second separation column is delivered to the same detector through the guide multi-channel valve for being detected.

2. The fluid separation method according to claim 1, wherein when the guide multi-channel valve is in the first mode, communication between the first separation column and the bypass line is in a closed status, communication between the first separation column and the second separation column, and communication between the second separation column and the detector are in a flow-through status, and the bypass line is in a loop closed status.

3. The fluid separation method according to claim 1, wherein when the guide multi-channel valve is in the second mode, communication between the first separation column and the second separation column is in a closed status, communication between the first separation column and the bypass line, and communication between the bypass line and the detector are in a flow-through status, and the second separation column is in a loop closed status.

4. The fluid separation method according to claim 1, wherein the process of providing the mixed fluid to the first separation column via the sampling entrance comprises:
    disposing a sampling loop, a carrier gas, and a sampling multi-channel valve, wherein the sampling loop is connected between the sampling entrance and the first separation column, the mixed fluid is delivered in a direction from the sampling entrance to the detector through the carrier gas, and the sampling multi-channel valve is disposed between the first separation column and the sampling entrance; and
    switching the sampling multi-channel valve to a sample inlet mode, wherein the mixed fluid filled in the sampling loop is delivered to the first separation column through the carrier gas.

5. The fluid separation method according to claim 4, wherein when the sampling multi-channel valve is in the sample inlet mode, communication between the sampling entrance and the sampling loop is in a closed status, communication between the carrier gas and the sampling loop, and communication between the sampling loop and the first separation column are in a flow-through status, and the carrier gas flows in a direction from the sampling loop to the first separation column.

6. The fluid separation method according to claim 4, wherein the sampling multi-channel valve further comprises a preset sampling mode, and when the sampling multi-channel valve is in the preset sampling mode, the mixed fluid flows in a flowing direction from the sampling entrance to the sampling loop, and the mixed fluid is filled in the sampling loop.

7. The fluid separation method according to claim 6, wherein when the sampling multi-channel valve is in the preset sampling mode, communication between the sampling entrance and the sampling loop is in a flow-through status, communication between the sampling entrance and the first separation column is in a closed status, and the carrier gas flows in a direction from an entrance of the first separation column to the detector.

8. The fluid separation method according to claim 1, wherein the first fluid does not flow through the second separation column.

9. The fluid separation method according to claim 1, wherein the first fluid comprises a polar gas of a group consisting of $CO_2$ and $H_2O$, and the second fluid comprises a non-polar gas of $H_2$.

10. The fluid separation method according to claim 1, further comprising:
    enabling a first part of the second fluid that is separated earlier to flow to the detector through the guide multi-channel valve in the first mode for being detected, before the guide multi-channel valve is switched from the first mode to the second mode;
    switching the guide multi-channel valve to the second mode before a first part of the first fluid that is separated earlier enters the second separation column, such that the first part of the first fluid that is separated earlier by the first separation column is detected by the detector through the guide multi-channel valve in the second mode and a second part of the second fluid is left in the second separation column for performing the separation procedure;
    switching the guide multi-channel valve to the first mode, such that a second part of the first fluid is still left in the first separation column and performs the separation procedure, and the second part of the second fluid left in the second separation column and already separated by the second separation column is delivered to the same detector through the guide multi-channel valve in the first mode for being detected; and
    switching the guide multi-channel valve to the second mode, such that the second part of the first fluid left in the first separation column and already separated by the first separation column is delivered to the same detector through the guide multi-channel valve in the second mode for being detected.

11. The fluid separation method according to claim 10, wherein the process of enabling the second part of the second fluid to perform the separation procedure in the second separation column further comprises performing a heating-up procedure.

12. The fluid separation method according to claim 10, wherein the first fluid comprises a polar gas of a group consisting of $CO_2$, $H_2O$, $CH_3OH$, and $C_2H_5OH$, the second fluid comprises a non-polar gas of $H_2$, $O_2$, $N_2$, $CH_4$, and CO, the first part of the first fluid is $CO_2$, the second part of the first fluid is $H_2O$, $CH_3OH$, and $C_2H_5OH$, the first part of the second fluid is $H_2$, $O_2$, and $N_2$, and the second part of the second fluid is $CH_4$ and CO.

13. A fluid separation apparatus, adapted to separate a mixed fluid with different properties, wherein the mixed fluid at least comprises a first fluid and a second fluid with different properties, the fluid separation apparatus comprising:
    a sampling entrance, wherein the mixed fluid flows via the sampling entrance;
    a first separation column, connected to the sampling entrance, and the first fluid is separated by the first separation column;
    a second separation column, connected to the first separation column in series, and the second fluid is separated by the second separation column;
    a bypass line, connected to the second separation column in parallel, and connected to the first separation column in series;
    a detector, connected to the second separation column and the bypass line, wherein the detector detects the first fluid and the second fluid being separated; and
    a guide multi-channel valve, comprising different modes to respectively control communication between the first separation column and the second separation column, communication between the first separation column and the bypass line, communication between the second separation column and the detector, and communication between the bypass line and the detector is in a flow-through status or a closed status.

14. The fluid separation apparatus according to claim 13, wherein the guide multi-channel valve comprises a first mode and a second mode, when the guide multi-channel valve is in the first mode, the mixed fluid flows in a flowing direction from the first separation column to the detector through the second separation column, and when the guide multi-channel valve is in the second mode, the mixed fluid flows in a flowing direction from the first separation column to the detector through the bypass line.

15. The fluid separation apparatus according to claim 14, wherein when the guide multi-channel valve is in the first mode, communication between the first separation column and the bypass line is in the closed status, communication between the first separation column and the second separation column, and communication between the second separation column and the detector are in the flow-through status, and the bypass line is in a loop closed status.

16. The fluid separation apparatus according to claim 14, wherein when the guide multi-channel valve is in the second mode, communication between the first separation column and the second separation column is in the closed status, communication between the first separation column and the bypass line, and communication between the bypass line and the detector are in the flow-through status, and the second separation column is in a loop closed status.

17. The fluid separation apparatus according to claim 13, further comprising a sampling loop and a carrier gas, wherein the sampling loop is connected between the sampling entrance and the first separation column, and the mixed fluid is delivered in a direction from the sampling entrance to the detector through the carrier gas.

18. The fluid separation apparatus according to claim 17, further comprising a sampling multi-channel valve, disposed between the first separation column and the sampling entrance, wherein the sampling multi-channel valve respectively controls communication between the sampling loop and the first separation column, communication between the sampling entrance and the sampling loop, communication between the carrier gas and the first separation column, and communication between the carrier gas and the sampling loop is in a flow-through status or a closed status.

19. The fluid separation apparatus according to claim 18, wherein the sampling multi-channel valve comprises a preset sampling mode and a sample inlet mode, when the sampling multi-channel valve is in the preset sampling mode, the mixed fluid flows in a flowing direction from the sampling entrance to the sampling loop, and the mixed fluid is filled in the sampling loop, and when the sampling multi-channel valve is in the sample inlet mode, the mixed fluid filled in the sampling loop is delivered to the first separation column through the carrier gas.

20. The fluid separation apparatus according to claim 19, wherein when the sampling multi-channel valve is in the preset sampling mode, communication between the sampling entrance and the sampling loop are in the flow-through status, communication between the sampling entrance and the first separation column is in the closed status, and the carrier gas flows in a direction from an entrance of the first separation column to the detector.

21. The fluid separation apparatus according to claim 19, wherein when the sampling multi-channel valve is in the sample inlet mode, communication between the sampling entrance and the sampling loop is in the closed status, communication between the carrier gas and the sampling loop, and communication between the sampling loop and communication between the first separation column are in the flow-through status, and the carrier gas flows in a direction from the sampling loop to the first separation column.

22. The fluid separation apparatus according to claim 13, wherein the first fluid and the second fluid are respectively a polar gas and a non-polar gas, the first separation column is a separation column for separating the polar gas, and the second separation column is a separation column for separating the non-polar gas.

* * * * *